United States Patent
Ehrhardt et al.

(10) Patent No.: US 7,374,899 B2
(45) Date of Patent: May 20, 2008

(54) SUCROSE-6-PHOSPHATE PHOSPHATASE AS TARGET FOR HERBICIDES

(75) Inventors: Thomas Ehrhardt, Speyer (DE); Uwe Sonnewald, Quedlinburg (DE); Frederik Börnke, Quedlinburg (DE); Shuai Chen, Gatersleben (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 303 days.

(21) Appl. No.: 10/522,096

(22) PCT Filed: Jul. 16, 2003

(86) PCT No.: PCT/EP03/07686

§ 371 (c)(1),
(2), (4) Date: Jan. 24, 2005

(87) PCT Pub. No.: WO2004/009808

PCT Pub. Date: Jan. 29, 2004

(65) Prior Publication Data

US 2006/0035786 A1     Feb. 16, 2006

(30) Foreign Application Priority Data

Jul. 23, 2002  (DE) ............................... 102 33 522

(51) Int. Cl.
    *C12Q 1/42*       (2006.01)
(52) U.S. Cl. ............... 435/21; 435/194; 435/252.3; 435/320.1; 536/23.2
(58) Field of Classification Search ............ 435/21, 435/194, 252.3, 320.1; 536/23.2
    See application file for complete search history.

(56) References Cited

U.S. PATENT DOCUMENTS 6,323,015 B1    11/2001   Orozco, Jr. et al.

FOREIGN PATENT DOCUMENTS

EP     1033405 A2     9/2000
WO     WO-01/79514 A2  10/2001

OTHER PUBLICATIONS

Effernick et al. [J. Bacteriol. Apr. 2001, p. 2405-2410].*
John E. Lunn (2003) "Sucrose-phosphatase Gene Families in Plants," Gene: An International Journal on Genes and Genomes, Elsevier Science Publishers, vol. 303, pp. 187-196.
Eccheveria et al. (1997) "Physical and Kinetic Evidence for an Association Between Sucrose-Phosphate Synthase and Sucrose-Phosphate Phosphatase," Plant Physiol., vol. 115, pp. 223-227.
Lunn et al. (2000) "Purification, Molecular Cloning and Sequence Analysis of Sucrose-6⁻—Phosphate Phosphohydrolase from Plants," Procl. Natl. Acad. Scie. vol. 97, No. 23, pp. 12914-12919.
Eccheveria et al. (1994) "Properties of Sucrose-Phosphate Phosphatase from Rice (*Orysa sativa*) Leaves," Plant Science, vol. 96, pp. 15-19.
David P. Whitaker (1984) "Purification and Properties of Sucrose-6-Phosphatase from Pisum Sativum Shoots," Phytochemistry, vol. 23, No. 11, pp. 2429-2430.
Bruce N. Ames (1956) "Assay of Inorganic Phosphate, Total Phosphate and Phosphatases," Analytical Methods, vol. 8, pp. 115-118.
S. Chifflet et al. (1988) "A Method for the Determination of Inorganic Phosphate in the Presence of Labile Organic Phosphate and High Concentrations of Protein: Application to Lens ATPases," Analytical Biochemistry, vol. 168, pp. 1-4.
Lanzetta et al. (1979) "An Improved Assay for Nanomole Amounts of Inorganic Phosphate," Analytical Biochemistry, vol. 100, pp. 95-97.
Uwe Sonnewald. (1992) "Expression of *E. coli* Inorganic Pyrophosphatase in Transgenic Plants Alters Photoassimilate Partitioning," The Plant Journal, vol. 2, No. 4, pp. 571-581.
F. Bornke et al. (2001) "Cloning and Characterization of the Gene Cluster for Palatinose Metabolism from the Phytopathogenic Bacterium *Erwinia rhapontici*," Journal of Bacteriology, vol. 183, No. 8, pp. 2425-2430.
Gen Bank Acc. No. AF283565 u. AAG31075, Nov. 11, 2000.
Gen Bank Acc. No. AF 434711 u. AAL30747, Nov. 14, 2001.
Gen Bank Acc. No. AG356816 u. AAK40235, Apr. 28, 2001.
Gen Bank Acc. No. AY029159 u. AAK31789, Apr. 17, 2001.
Gen Bank Acc. No. AF321557 u. AAK09372, Feb. 19, 2001.
Gen Bank Acc. No. AF321556 u. AAK09371, Feb. 19, 2001.
Gen Bank Acc. No. AF283566 u. AAG31076, Nov. 11, 2000.
Gen Bank Acc. No. AAG31074, Jan. 10, 2001.

* cited by examiner

*Primary Examiner*—Tekchand Saidha
(74) *Attorney, Agent, or Firm*—Hutchison Law Group PLLC

(57) ABSTRACT

The present invention relates to the use of a polypeptide with the biological activity of a sucrose-6-phosphate phosphatase which, if not present, brings about growth retardation symptoms and chlorotic leaves and which is encoded by the nucleic acid sequences SEQ ID NO:1, SEQ ID NO:3, SEQ ID NO:5 or by a functional equivalent of SEQ ID NO:1, SEQ ID NO:3 or SEQ ID NO:5 as target for herbicides. Moreover, the present invention relates to the use of the abovementioned polypeptides in a method for identifying herbicidal or growth-regulatory compounds which inhibit sucrose-6-phosphate phosphatase. Moreover, the invention relates to the use of these compounds which have been identified via the method as herbicides or growth regulators.

8 Claims, No Drawings

SUCROSE-6-PHOSPHATE PHOSPHATASE AS TARGET FOR HERBICIDES

FIELD OF THE INVENTION

The present invention relates to the use of a polypeptide with the biological activity of sucrose-6-phosphate phosphatase which, if not present, brings about growth retardation symptoms and chlorotic leaves and which is encoded by the nucleic acid sequences SEQ ID NO:1, SEQ ID NO:3, SEQ ID NO:5 or by a functional equivalent of SEQ ID NO:1, SEQ ID NO:3 or SEQ ID NO:5 as target for herbicides. Moreover, the present invention relates to the use of the abovementioned polypeptides in a method for identifying herbicidal or growth-regulatory compounds which inhibit sucrose-6-phosphate phosphatase. Moreover, the invention relates to the use of these compounds which have been identified via the method as herbicides or growth regulators.

BACKGROUND OF THE INVENTION

The basic principle of identifying herbicides via inhibiting a defined target is known (for example U.S. Pat. No. 5,187,071, WO 98/33925, WO 00/77185). In general, there is a great demand for the detection of enzymes which might constitute novel targets for herbicides. Reasons for this are that herbicidal active ingredients which act on known targets demonstrate the development of resistance problems, and the constant endevor to identify novel herbicidal active ingredients which are distinguished by as broad as possible a range of action, environmental friendliness and toxicological compatibility and/or low application rates.

In practice, the detection of novel targets always entails great difficulties since the inhibition of an enzyme which is part of a metabolic pathway frequently has no further effects on the plant's growth. The reason may be that the plant switches over to alternative metabolic pathways whose existence is not known, or that the enzyme which is being inhibited is not limiting for the metabolic pathway. Furthermore, plant genomes are distinguished by a high degree of functional redundancy. In the *Arabidopsis thaliana* genome, functionally equivalent enzymes are more frequently found in gene families than is the case with insects or mammals (Nature, 2000, 408(6814):796-815). This hypothesis is confirmed experimentally by the fact that large gene knock-out programs by means of the insertion of T-DNA or transposons into *Arabidopsis* have, as yet, yielded fewer manifested phenotypes than expected (Curr. Op. Plant Biol. 4, 2001, pp. 111-117).

SUMMARY OF THE INVENTION

It is an object of the present invention to identify novel targets which are essential for the growth of plants or whose inhibition leads to reduced plant growth, and to provide methods which are suitable for identifying herbicidally active compounds.

We have found that this object is achieved by the use of a polypeptide with the biological activity of a sucrose-6-phosphate phosphatase encoded by a nucleic acid sequence comprising:

a) a nucleic acid sequence with the nucleic acid sequence shown in SEQ ID NO:1, SEQ ID NO:3 or SEQ ID NO:5; or b) a nucleic acid sequence which, on the basis of the degeneracy of the genetic code, can be derived from the amino acid sequence shown in SEQ ID NO:2, SEQ ID NO:4 or SEQ ID NO:6 by back translation; or c) functional equivalents of the nucleic acid sequence SEQ ID NO:1 with at least 55% identity with SEQ ID NO:1; or functional equivalents of the nucleic acid sequence SEQ ID NO:3 with at least 55% identity with SEQ ID NO:3; or functional equivalents of the nucleic acid sequence SEQ ID NO:5 with at least 51% identity with SEQ ID NO:5; or d) a nucleic acid sequence which, on the basis of the degeneracy of the genetic code, can be derived from the amino acid sequence of a functional equivalent of SEQ ID NO:2 with at least 55% identity with SEQ ID NO:2 by back translation; or a nucleic acid sequence which, on the basis of the degeneracy of the genetic code, can be derived from the amino acid sequence of a functional equivalent of SEQ ID NO:4 with at least 54% identity with SEQ ID NO:4 by back translation; or a nucleic acid sequence which, on the basis of the degeneracy of the genetic code, can be derived from the amino acid sequence of a functional equivalent of SEQ ID NO:6 with at least 54% identity with SEQ ID NO:6 by back translation;

as targets for herbicides.

Further terms used in the specification are now defined at this point.

"Affinity tag": This refers to a peptide or polypeptide whose coding nucleic acid sequence can be fused to the nucleic acid sequence according to the invention either directly or by means of a linker, using customary cloning techniques. The affinity tag serves for the isolation, concentration and/or specific purification of the recombinant target protein by means of affinity chromatography from total cell extracts. The abovementioned linker can advantageously contain a protease cleavage site (for example for thrombin or factor Xa), whereby the affinity tag can be cleaved from the target protein when required. Examples of common affinity tags are the "His tag", for example from Quiagen, Hilden, the "Strep tag", the "Myc tag" (Invitrogen, Carlsberg), the tag from New England Biolabs which consists of a chitin-binding domain and an intein, the maltose-binding protein (pMal) from New England Biolabs, and what is known as the CBD tag from Novagen. In this context, the affinity tag can be attached to the 5' or the 3' end of the coding nucleic acid sequence with the sequence encoding the target protein.

"Expression cassette": An expression cassette contains a nucleic acid sequence according to the invention linked operably to at least one genetic control element, such as a promoter, and, advantageously, a further control element, such as a terminator. The nucleic acid sequence of the expression casette can be, for example, a genomic or complementary DNA sequence or an RNA sequence, and the semisynthetic or fully synthetic analogs thereof. These sequences can exist in linear or circular form, extrachromosomally or integrated into the genome. The nucleic acid sequences in question can be synthesized or obtained naturally or comprise a mixture of synthetic and natural DNA components, and consist of a variety of heterologous gene segments from various organisms.

Artificial nucleic acid sequences are also suitable in this context as long as they make possible the expression, in a cell or organism, of a polypeptide encoded by a nucleic acid sequence according to the invention and having the biological activity of a sucrose-6-phosphate phosphatase. For example, synthetic nucleotide sequences can be generated which have been optimized with regard to the codon usage of the organisms to be transformed.

All of the abovementioned nucleotide sequences can be generated from the nucleotide units by chemical synthesis in the manner known per se, for example by fragment condensation of individual, overlapping complementary nucleotide units of the double helix. Oligonucleotides can be synthesized chemically for example in the manner known per se using the phosphoamidite method (Voet, Voet, 2$^{nd}$ Edition, Wiley Press New York, pp. 896-897). When preparing an expression cassette, various DNA fragments can be manipulated in such a way that a nucleotide sequence with the correct direction of reading and the correct reading frame is obtained. The nucleic acid fragments are linked to each other via general cloning techniques as are described, for example, in T. Maniatis, E. F. Fritsch and J. Sambrook, "Molecular Cloning: A Laboratory Manual", Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., "Current Protocols in Molecular Biology", Greene Publishing Assoc. and Wiley-Interscience (1994).

"Operable linkage": An operable, or functional, linkage is understood as meaning the sequential arrangement of regulatory sequences or genetic control elements in such a way that each of the regulatory sequences, or each of the genetic control elements, can fulfill its intended function when the coding sequence is expressed.

"Functional equivalents" describe, in the presence context, nucleic acid sequences which hybridize under standard conditions with the nucleic acid sequence SEQ ID NO:1, SEQ ID NO:3 or SEQ ID NO:5 or parts of SEQ ID NO:1, SEQ ID NO:3 or SEQ ID NO:5 and which are capable of bringing about the expression, in a cell or an organism, of a polypeptide with the biological activity of a sucrose-6-phosphate phosphatase.

To carry out the hybridization, it is advantageous to use short oligonucleotides with a length of approximately 10-50 bp, preferably 15-40 bp, for example of the conserved or other regions, which can be determined in the manner with which the skilled worker is familiar by comparisons with other related genes. However, longer fragments of the nucleic acids according to the invention with a length of 100-500 bp, or the complete sequences, may also be used for hybridization. Depending on the nucleic acid/oligonucleotide used, and the length of the fragment or of the complete sequence, or depending on which type of nucleic acid, i.e. DNA or RNA, is being used for the hybridization, these standard conditions vary. Thus, for example, the melting points for DNA:DNA hybrids are approximately 10° C. lower than those of DNA:RNA hybrids of the same length.

Standard hybridization conditions are to be understood as meaning, depending on the nucleic acid, for example temperatures of between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids are advantageously 0.1×SSC and temperatures of between about 20° C. and 65° C., preferably between approximately 30° C. and 45° C. In the case of DNA:RNA hybrids, the hybridization conditions are advantageously 0.1×SSC and temperatures of between approximately 30° C. and 65° C., preferably between approximately 45° C. and 55° C. These hybridization temperatures which have been stated are the melting temperature values calculated for example for a nucleic acid with a length of approximately 100 nucleotides and a G+C content of 50% in the absence of formamide. The experimental conditions for the hybridization of DNA are described in specialist textbooks of genetics such as, for example, in Sambrook et al., "Molecular Cloning", Cold Spring Harbor Laboratory, 1989, and can be calculated using formulae with which the skilled worker is familiar, for example as a function of the length of the nucleic acids, the type of the hybrids or the G+C content. The skilled work will find further information on hybridization in the following textbooks: Ausubel et al. (eds), 1985, "Current Protocols in Molecular Biology", John Wiley & Sons, New York; Hames and Higgins (eds), 1985, "Nucleic Acids Hybridization: A Practical Approach", IRL Press at Oxford University Press, Oxford; Brown (ed), 1991, Essential Molecular Biology: A Practical Approach, IRL Press at Oxford University Press, Oxford.

A functional equivalent of SEQ ID NO:1, SEQ ID NO:3 or SEQ ID NO:5 is furthermore also understood as meaning nucleic acid sequences which have a defined degree of homology or identity with SEQ ID NO:1, SEQ ID NO:3 or SEQ ID NO:5, and furthermore in particular also natural or artificial mutations of the abovementioned nucleic acid sequences which encode a polypeptide with the biological activity of a sucrose-6-phosphate phosphatase.

Thus, the present invention also encompasses, for example, those nucleotide sequences which are obtained by modification of the abovementioned nucleic acid sequences. For example, such modifications can be generated by techniques with which the skilled worker is familiar, such as "site directed mutagenesis", "error prone PCR", "DNA shuffling" (Nature 370, 1994, pp. 389-391) or "staggered extension process" (Nature Biotechnol. 16, 1998, pp. 258-261). The purpose of such a modification can be, for example, the insertion of further cleavage sites for restriction enzymes, the removal of DNA in order to truncate the sequence, the substitution of nucleotides in order to optimize the codons, or the addition of further sequences. Proteins which are encoded via modified nucleic acid sequences must retain the desired functions despite a deviating nucleic acid sequence.

The term "functional equivalent" may also relate to the amino acid sequence encoded by the nucleic acid sequence in question. In this case, the term "functional equivalent" describes a protein whose amino acid sequence has up to a defined degree of identity or homology with SEQ ID NO:2, SEQ ID NO:4 or SEQ ID NO:6.

Functional equivalents thus comprise naturally occuring variants of the herein-described sequences and artificial nucleic acid sequences, for example those which have been obtained by chemical synthesis and which are adapted to the codon usage, and also the amino acid sequences derived from them.

The term "genetic control sequence" describes sequences which have an effect on the transcription and, if appropriate, translation of the nucleic acids according to the invention in prokaryotic or eukaryotic organisms. Examples are promoters, terminators or what are known as "enhancer" sequences. In addition to these control sequences, or instead of these sequences, the natural regulation of these sequences may still be present before the actual structural genes and may, if appropriate, have been modified genetically in such a way that the natural regulation has been switched off and the expression of the target gene has been modified, that is to say increased or reduced. The choice of the control sequence depends on the host organism or starting organism. Genetic control sequences furthermore also comprise the 5'-untranslated region, introns or the noncoding 3' region of genes. Control sequences are furthermore understood as meaning those which make possible a homologous recombination or insertion into the genome of a host organism or which permit the removal from the genome. Genetic control sequences also comprise further promoters, promoter elements or minimal promoters, and sequences which have an effect on chromatin structure (for example matrix attachment regions (MARs)), which are capable of modifying the expression-governing properties. Thus, genetic control sequences may bring about for example the fact that the tissue-specific expression is additionally dependent on certain stress factors. Such elements have been described, for example, for water stress, abscisic acid (Lam E and Chua N H, J Biol Chem 1991; 266(26): 17131-17135), cold stress and dry stress (Plant Cell 1994, (6): 251-264) and heat stress (Molecular & General Genetics, 1989, 217(2-3): 246-53).

"Homology" between two nucleic acid sequences or polypeptide sequences is defined by the identity of the nucleic acid sequence/polypeptide sequence over in each case the entire sequence length, which is calculated by alignment with the aid of the program algorithm ClustalW (Thompson, J. D., Higgins, D. G. and Gibson, T. J. (1994) Nucleic Acids Res. 22:4673-80), setting the following parameters:

GAP Penalty 15.00 DNA transition weight: 0.5
GAP Length Penalty 6.66 Protein weight matrix: Gonnet Series
Delay divergent Seqs (%) 30 DNA weight matrix: IUB In the following text, the term identity is also used synonymously instead of the term "homologous" or "homology".

"Mutations" of nucleic acid sequences or amino acid sequences comprise substitutions, additions, deletions, inversions or insertions of one or more nucleotide residues, which may also bring about changes in the corresponding amino acid sequence of the target protein by the substitution, insertion or deletion of one or more amino acids, but where the functional properties of the target proteins in total are essentially retained.

"Natural genetic environment" refers to the natural chromosomal locus in the organism of origin. In the case of a genomic library, the natural genetic environment of the nucleic acid sequence is preferably obtained at least in part. The environment flanks the nucleic acid sequence at least at 5' or 3' and has a sequence length of at least 50 bp, preferably at least 100 bp, especially preferably at least 500 bp, very especially preferably at least 1000 bp, most preferably at least 5000 bp.

"Plants" for the purposes of the invention are plant cells, plant tissues, plant organs or intact plants, such as seeds, tubers, flowers, pollen, fruits, seedlings, roots, leaves, stems or other plant parts. Moreover, the term plants is understood as meaning propagation material such as seeds, fruits, seedlings, slips, tubers, cuttings or rootstocks.

"Reaction time" refers to the time required for carrying out an activity assay until a significant finding regarding an activity is obtained; it depends both on the specific activity of the protein employed in the assay and on the method used and the sensitivity of the apparatus used. The skilled worker is familiar with the determination of the reaction times. In the case of methods for identifying herbicidally active compounds which are based on photometry, the reaction times are, in general, for example between >0 to 120 minutes.

"Recombinant DNA" describes a combination of DNA sequences which can be generated by recombinant DNA technology.

"Recombinant DNA technology": generally known techniques for fusing DNA sequences (for example described in Sambrook et al., 1989, Cold Spring Habour, N.Y., Cold Spring Habour Laboratory Press).

"Replication origins" ensure the multiplication of the expression cassettes or vectors according to the invention in microorganisms and yeasts, for example the pBR322 ori or the P15A ori in *E. coli* (Sambrook et al.: "Molecular Cloning. A Laboratory Manual", 2nd ed. Cold Spring Harbor Laboratory Press, Cold Spring Harbor, N.Y., 1989) and the ARS1 ori in yeast (Nucleic Acids Research, 2000, 28(10): 2060-2068).

"Reporter genes" encode readily quantifiable proteins. The transformation efficacy or the expression site or timing can be assessed by means of these genes via growth assay, fluorescence assay, chemoluminescence assay, bioluminescence assay or resistance assay or via a photometric measurement (intrinsic color) or enzyme activity. Very especially preferred in this context are reporter proteins (Schenborn E, Groskreutz D. Mol Biotechnol. 1999; 13(1): 29-44) such as "green fluorescence protein" (GFP) (Gerdes H H and Kaether C, FEBS Lett. 1996; 389(1):44-47; Chui W L et al., Curr Biol 1996, 6:325-330; Leffel S M et al., Biotechniques. 23(5):912-8, 1997), chloramphenicol acetyltransferase, a luciferase (Giacomin, Plant Sci 1996, 116:59-72; Scikantha, J Bact 1996, 178:121; Millar et al., Plant Mol Biol Rep 1992 10:324-414), and luciferase genes, in general β-galactosidase-or β-glucuronidase (Jefferson et al., EMBO J. 1987, 6, 3901-3907) or the Ura3 gene.

"Selection markers" confer a resistance to antibiotics or other toxic compounds: examples which may be mentioned in this context are the neomycin phosphotransferase gene, which confers resistance to the aminoglycoside antibiotics neomycin (G 418), kanamycin, paromycin (Deshayes A et al., EMBO J. 4 (1985) 2731-2737), the sul gene, which encodes a mutated dihydropteroate synthase (Guerineau F et al., Plant Mol Biol. 1990; 15(1):127-136), the hygromycin B phosphotransferase gene (GenBank Accession No: K 01193) and the shble resistance gene, which confers resistance to the bleomycin antibiotics such as, for example, zeocin. Further examples for selection marker genes are genes which confer resistance to 2-deoxyglucose-6-phosphate (WO 98/45456) or phosphinothricin and the like or those which confer resistance to antimetabolites, for example the dhfr gene (Reiss, Plant Physiol. (Life Sci. Adv.) 13 (1994) 142-149). Others which are suitable are genes such as trpB or hisD (Hartman S C and Mulligan R C, Proc Natl Acad Sci U S A. 85 (1988) 8047-8051). Another suitable gene is the mannose-phosphate isomerase gene (WO 94/20627), the ODC (ornithin decarboxylase) gene (McConlogue, 1987 in: Current Communications in Molecular Biology, Cold Spring Harbor Laboratory, Hrsg.) or the *Aspergillus terreus* deaminase (Tamura K etal., Biosci Biotechnol Biochem. 59 (1995) 2336-2338).

"Transformation" describes a process for introducing heterologous DNA into a prokaryotic or eukaryotic cell. The term transformed cell describes not only the product of the transformation process per se, but also all of the transgenic progeny of the transgenic organism generated by the transformation.

"Target/target protein": a polypeptide encoded via the nucleic acid sequence according to the invention, which may take the form of an enzyme in the traditional sense or, for example, of a structural protein, a protein which is relevant for developmental processes, regulatory proteins such as transcription factors, kinases, phosphatases, receptors, channel subunits, transport proteins, regulatory subunits which confer substrate or activity regulation to an enzyme complex. All of the targets or sites of action show that their functional presence is essential for the survival or the normal development and growth.

"Transgenic": referring to a nucleic acid sequence, an expression cassette or a vector comprising a nucleic acid sequence according to the invention or an organism transformed with the abovementioned nucleic acid sequence, expression cassette or vector, the term transgenic describes all those constructs which have been generated by recombinant methods in which either the nucleic acid sequence of the target protein or a genetic control sequence linked operably to the nucleic acid sequence of the target protein or a combination of the abovementioned possibilities are not in their natural genetic environment or have been modified by recombinant methods. In this context, modification can be achieved for example by mutating one or more nucleotide residues of the nucleic acid sequence in question.

Sucrose-6-phosphate phosphatase, a sucrose biosynthesis enzyme which is localized in the cytosol, catalyzes the conversion of sucrose-6-phosphate into orthophosphate and sucrose. An enzyme with the biological activity of a sucrose-6-phosphate phosphatase thus describes an enzyme which is capable of catalyzing the above-described reaction. Corresponding activity assays are described further below. Sucrose-6-phosphate is a product of the reaction in which UDP-glucose and fructose-6-phosphate are converted into sucrose-6-phosphate and which is catalyzed by sucrose-6-phosphate synthase. More recent data suggest an association of sucrose-6-phosphate synthase and sucrose-6-phosphate phosphatase in a protein complex (Eccheveria et al. 1997, Plant Physiology 115, 223), which might suggest that sucrose-6-phosphate phosphatase has a regulatory function. It is not known whether sucrose-6-phosphate phosphatase is essential for the plant or not.

The cloning of sucrose-6-phosphate phosphatase-encoding genes from a variety of plant species has been described in the literature (Lunn et al., 2000, Procl. Natl. Acad. Sci. USA 97: 12914), but no studies into the in-planta function of the enzyme have been performed.

The following are known: three sucrose-6-phosphate phosphatase-encoding nucleic acid sequences and protein sequences from *Arabidopsis thaliana*, GenBank Acc. No AF 283565 and AAG31075 (identity with SEQ ID NO:1=68%; identity with SEQ ID NO:2=72%; identity with SEQ ID NO:3=68%; identity with SEQ ID NO:4=72%; identity with SEQ ID NO:5=61%; identity with SEQ ID NO:6=71%), GenBank Acc. No. AF434711 and AAL30747 (identity with SEQ ID NO:1=55%; identity with SEQ ID NO:2=55%; identity with SEQ ID NO:3=56%; identity with SEQ ID NO:4=54%; identity with SEQ ID NO:5=51%; identity with SEQ ID NO:6=54%) and GenBank Acc. No. AF356816 and AAK40235 (identity with SEQ ID NO:1=62%; identity with SEQ ID NO:2=60%; identity with SEQ ID NO:3=63%; identity with SEQ ID NO:4=61%; identity with SEQ ID NO:5=59%, identity with SEQ ID NO:6=60%), three sucrose-6-phosphate phosphatase encoding nucleic acid sequences from *Triticum aestivum*, GenBank Acc. No AY029159 and AAK31789 (identity with SEQ ID NO:1=62%; identity with SEQ ID NO:2=64%; identity with SEQ ID NO:3=61%; identity with SEQ ID NO:4=64%; identity with SEQ ID NO:5=56%; identity with SEQ ID NO:6=64%), GenBank Acc. No. AF321557 and AAK09372 (identity with SEQ ID NO:1=61%; identity with SEQ ID NO:2=64%; identity with SEQ ID NO:3=60%; identity with SEQ ID NO:4=64%; identity with SEQ ID NO:5=60%; identity with SEQ ID NO:6=64%) and GenBank Acc. No. AF321556 and AAK09371 (identity with SEQ ID NO:1=67%; identity with SEQ ID NO:2=64%; identity with SEQ ID NO:3=60%; identity with SEQ ID NO:4=64%; identity with SEQ ID NO:5=61%; identity with SEQ ID NO:6=64%), one sucrose-6-phosphate phosphatase-encoding nucleic acid sequence from Medicago trunculata, GenBank Acc. No AF283566 and AAG31076 (identity with SEQ ID NO:1=67%; identity with SEQ ID NO:2=67%; identity with SEQ ID NO:3=67%; identity with SEQ ID NO:4=69%; identity with SEQ ID NO:5=62%; identity with SEQ ID NO:6=66%) and one sucrose-6-phosphate phosphatase-encoding nucleic acid sequence from *Zea mays*, GenBank Acc. No AAG31074 (identity with SEQ ID NO:2=62%; identity with SEQ ID NO:4=63%; identity with SEQ ID NO:6=63%).

Surprisingly, it has been found within the scope of the present invention that plants in which the activity of sucrose-6-phosphate phosphatase was specifically reduced, exhibited phenotypes which are comparable with phenotypes generated by the application of herbicides. Among the symptoms observed were growth retardation symptoms and chlorotic leaves, and, in some cases, the death of entire plants or of plant parts.

The present invention relates to use of a polypeptide with the biological activity of a sucrose-6-phosphate phosphatase encoded by a nucleic acid sequence comprising:

a) a nucleic acid sequence with the nucleic acid sequence shown in SEQ ID NO:1, SEQ ID NO:3 or SEQ ID NO:5; or b) a nucleic acid sequence which, on the basis of the degeneracy of the genetic code, can be derived from the amino acid sequence shown in SEQ ID NO:2, SEQ ID NO:4 or SEQ ID NO:6 by back translation; or c) functional equivalents of the nucleic acid sequence SEQ ID NO:1 with at least 55% identity with SEQ ID NO:1; or functional equivalents of the nucleic acid sequence SEQ ID NO:3 with at least 55% identity with SEQ ID NO:3; or functional equivalents of the nucleic acid sequence SEQ ID NO:5 with at least 51% identity with SEQ ID NO:5; or d) a nucleic acid sequence which, on the basis of the degeneracy of the genetic code, can be derived from the amino acid sequence of a functional equivalent of SEQ ID NO:2 with at least 55% identity with SEQ ID NO:2 by back translation; or a nucleic acid sequence which, on the basis of the degeneracy of the genetic code, can be derived from the amino acid sequence of a functional equivalent of SEQ ID NO:4 with at least 54% identity with SEQ ID NO:4 by back translation; or a nucleic acid sequence which, on the basis of the degeneracy of the genetic code, can be derived from the amino acid sequence of a functional equivalent of SEQ ID NO:6 with at least 54% identity with SEQ ID NO:6 by back translation;

as target for herbicides. a functional equivalent of c) and d) are distinguished by the same functionality, i.e. they have the physiological function of a sucrose-6-phosphate phosphatase.

The abovementioned nucleic acid sequences preferably originate from a plant, for example a plant from the family of the Solanaceae.

The functional equivalents according to the invention of SEQ ID NO:1 have at least 55%, 56%, 57%, 58%, 59%, 60%, 61%, 62%, 63%, 64%, 65%, 66%, 67%, 68%, by preference at least 69%, 70%, 71%, 72%, 73%, 74%, by preference at least 75%, 76%, 77%, 78%, 79%, 80%, 81%, 82%, 83%, by preference at least 84%, 85%, 86%, 87%, 88%, 89%, 90%, 91%, 92%, 93%, especially preferably at least 94%, 95%, 96%, 97%, 98%, 99% homology with SEQ ID NO:1.

The functional equivalents according to the invention of SEQ ID NO:2 have at least 55%, 56%, 57%, 58%, 59%, 60%, 61%, 62%, 63%, 64%, by preference at least 65%, 66%, 67%, 68%, 69%, 70%, 71%, 72%, by preference at least 73%, 74%, 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% homology with SEQ ID NO:2.

The functional equivalents according to the invention of SEQ ID NO:3 have at least 55%, 56%, 57%, 58%, 59%, 60%, 61%, 62%, 63%, 64%, 65%, 66%, 67%, 68%, by preference at least 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% homology with SEQ ID NO:3.

The functional equivalents of SEQ ID NO:4 according to the invention have at least 54%, 55%, 56%, 57%, 58%, 59%, 60%, 61%, 62%, by preference at least 63%, 64%, 65%, 66%, 67%, 68%, 69%, 70%, 71%, 72%, by preference at least 73%, 74%, 75%, 76%, 77%, 78%, 79%, 80%, 81%, 82%, preferably at least 83%, 84%, 85%, 86%, 87%, 88%, 89%, 90%, 91%, 92%, 93%, especially preferably at least 94%, 95%, 96%, 97%, 98%, 99% homology with SEQ ID NO:4.

The functional equivalents of SEQ ID NO:5 according to the invention have at least 51%, 52%, 53%, 54%, 55%, 56%, 57%, 58%, 59%, 60%, 61%, 62%, by preference at least 63%, 64%, 65%, 66%, 67%, 68%, 69%, 70%, 71%, 72%, 73%, 74%, by preference at least 75%, 76%, 77%, 78%, 79%, 80%, 81%, 82%, 83%, by preference at least 84%, 85%, 86%, 87%, 88%, 89%, 90%, 91%, 92%, 93% especially preferably at least 94%, 95%, 96%, 97%, 98%, 99% homology with SEQ ID NO:5.

The functional equivalents of SEQ ID NO:6 according to the invention have at least 54%, 55%, 56%, 57%, 58%, 59%, 60%, 61%, 62%, 63%, 64%, by preference at least 65%, 66%, 67%, 68%, 69%, 70%, 71%, by preference at leat 72%, 73%, 74%, 75%, 76%, 77%, 78%, 79%, 80%, 81%, 82%, 83%, by preference at least 84%, 85%, 86%, 87%, 88%, 89%, 90%, 91%, 92%, 93%, especially preferably at least 94%, 95%, 96%, 97%, 98%, 99% homology with SEQ ID NO:6.

Examples of functional equivalents in accordance with c) and d) are the nucleic acid sequences which encode sucrose-6-phosphate phosphatase and which have already been mentioned above, and protein sequences from *Arabidopsis thaliana* (Gen. Bank Acc. No AF 283565 and AAG31075, Gen. Bank Acc. No. AF434711 and AAL30747; Gen. Bank Acc. No. AF356816 and AAK40235), the three nucleic acid sequences from *Triticum aestivum* which encode sucrose-6-phosphate phosphatase (Gen. Bank Acc. No. AY029159 and AAK31789, Gen. Bank Acc. No. AF321557 and AAK09372; Gen. Bank Acc. No. AF321556 and AAK09371), the nucleic acid sequence from *Medicago truncatula* which encodes sucrose-6-phosphate phosphatase (Gen. Bank Acc. No. AF283566 and AAG31076) and the nucleic acid sequence from *Zea mays* which encodes sucrose-6-phosphate phosphatase (Gen. Bank Acc. No. AAG31074).

Furthermore claimed within the scope of the present invention are nucleic acid sequences encoding a polypeptide with the biological activity of a sucrose-6-phosphat phosphatase comprising:

a) a nucleic acid sequence with the nucleic acid sequence shown in SEQ ID NO:1, SEQ ID NO:3 or SEQ ID NO:5; or b) a nucleic acid sequence which, on the basis of the degeneracy of the genetic code, can be derived from the amino acid sequence shown in SEQ ID NO:2, SEQ ID NO:4 or SEQ ID NO:6 by back translation; or c) functional equivalents of the nucleic acid sequence SEQ ID NO:1 with at least 69% identity with SEQ ID NO:1; or functional equivalents of the nucleic acid sequence SEQ ID NO:3 with at least 69% identity with SEQ ID NO:3; or functional equivalents of the nucleic acid sequence SEQ ID NO:5 with at least 63% identity with SEQ ID NO:5; or d) a nucleic acid sequence which, on the basis of the degeneracy of the genetic code, can be derived from the amino acid sequence of a functional equivalent of SEQ ID NO:2 with at least 73% identity with SEQ ID NO:2 by back translation; or a nucleic acid sequence which, on the basis of the degeneracy of the genetic code, can be derived from the amino acid sequence of a functional equivalent of SEQ ID NO:4 with at least 73% identity with SEQ ID NO:4 by back translation; or a nucleic acid sequence which, on the basis of the degeneracy of the genetic code, can be derived from the amino acid sequence of a functional equivalent of SEQ ID NO:6 with at least 72% identity with SEQ ID NO:6 by back translation.

The abovementioned nucleic acid sequences originate from a plant, for example from a plant of the family of the Solanaceae.

The polypeptides encoded by the abovementioned nucleic acid sequences are likewise claimed. The functional equivalents of c) and d) are distinguished by the same functionality, i.e. they have the physiological function of a sucrose-6-phosphate phosphatase.

The functional equivalents of SEQ ID NO:1 according to the invention have at least 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:1.

The functional equivalents of SEQ ID NO:2 according to the invention have at least 73%, by preference at least 74%, 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:2.

The functional equivalents of SEQ ID NO:3 according to the invention have at least 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:3.

The functional equivalents of SEQ ID NO:4 according to the invention have at least 73%, by preference at least 74%, 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:4.

The functional equivalents of SEQ ID NO:5 according to the invention have at least 63%, 64%, 65%, 66%, 67%, 68%, 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:5.

The functional equivalents of SEQ ID NO:6 according to the invention have at least 72%, 73%, by preference at least 74%, 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% identity with SEQ ID NO:6.

The nucleic acid sequences encoding a polypeptide with the biological activity of a sucrose-6-phosphate phosphatase comprising a) a nucleic acid sequence with the nucleic acid sequence shown in SEQ ID NO:1, SEQ ID NO:3 or SEQ ID NO:5; or
b) a nucleic acid sequence which, on the basis of the degeneracy of the genetic code, can be derived from the amino acid sequence shown in SEQ ID NO:2, SEQ ID NO:4 or SEQ ID NO:6 by back translation; or
c) functional equivalents of the nucleic acid sequence SEQ ID NO:1 with at least 55% identity with SEQ ID NO:1; or functional equivalents of the nucleic acid sequence SEQ ID NO:3 with at least 55% identity with SEQ ID NO:3; or functional equivalents of the nucleic acid sequence SEQ ID NO:5 with at least 51% identity with SEQ ID NO:5; or
d) functional equivalents of the nucleic acid sequence SEQ ID NO:1 with at least 69% identity with SEQ ID NO:1; or functional equivalents of the nucleic acid sequence SEQ ID NO:3 with at least 69% identity with SEQ ID NO:3; or functional equivalents of the nucleic acid sequence SEQ ID NO:5 with at least 63% identity with SEQ ID NO:5; or
e) a nucleic acid sequence which, on the basis of the degeneracy of the genetic code, can be derived from the amino acid sequence of a functional equivalent of SEQ ID NO:2 with at least 73% identity with SEQ ID NO:2 by back translation; or a nucleic acid sequence which, on the basis of the degeneracy of the genetic code, can be derived from the amino acid sequence of a functional equivalent of SEQ ID NO:4 with at least 73% identity with SEQ ID NO:4 by back translation; or a nucleic acid sequence which, on the basis of the degeneracy of the genetic code, can be derived from the amino acid sequence of a functional equivalent of SEQ ID NO:6 with at least 72% identity with SEQ ID NO:6 by back translation; or
f) a nucleic acid sequence which, on the basis of the degeneracy of the genetic code, can be derived from the amino acid sequence of a functional equivalent of SEQ ID NO:2 with at least 55% identity with SEQ ID NO:2 by back translation; or a nucleic acid sequence which, on the basis of the degeneracy of the genetic code, can be derived from the amino acid sequence of a functional equivalent of SEQ ID NO:4 with at least 54% identity with SEQ ID NO:4 by back translation; or a nucleic acid sequence which, on the basis of the degeneracy of the genetic code, can be derived from the amino acid sequence of a functional equivalent of SEQ ID NO:6 with at least 54% identity with SEQ ID NO:6 by back translation;

are referred to hereinbelow as "nucleic acid sequences according to the invention". For the sake of simplicity, the polypeptides with the biological activity of a sucrose-6-phosphate phosphatase which are encoded by a nucleic acid sequence according to the invention are hereinbelow referred to as "SSP".

Reduced amounts of SSPs bring about growth rate retardation symptoms and necrotic leaves in plants. A reduction in the polypeptide means that the amount of polypeptide is reduced via recombinant methods. A plant which has been modified thus is compared with a plant which has not been genetically modified with regard to this polypeptide, but which is otherwise identical with the genotype of the genetically manipulated plant under identical growth conditions.

The gene products of the nucleic acids according to the invention constitute novel targets for herbicides which make it possible to provide novel herbicides for controlling undesired plants.

Undesired plants are understood as meaning, in the broadest sense, all those plants which grow at locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

SEQ ID NO:1, SEQ ID NO:3 or SEQ ID NO:5 or parts of the abovementioned nucleic acid sequences can be used for the preparation of hybridization probes, by means of which the corresponding full-length genes or functional equivalents of SEQ ID NO:1, SEQ ID NO:3 or SEQ ID NO:5 can be isolated. The preparation of these probes and the experimental procedure are known. For example, this can be effected via the tailor-made preparation of radioactive or nonradioactive probes by means of PCR and the use of suitably labeled oligonucleotides, followed by hybridization experiments. The technologies required for this purpose are given, for example, in T. Maniatis, E. F. Fritsch and J. Sambrook, "Molecular Cloning: A Laboratory Manual", Cold Spring Harbor Laboratory, Cold Spring Harbor, N.Y. (1989). The probes in question can furthermore be modified by standard technology (lit. SDM or random mutagenesis) in such a way that they can be employed for other purposes, for example as probe which hybridizes specifically with mRNA and the corresponding coding sequences in order to analyze the corresponding sequences in other organisms.

Moreover, the abovementioned probes can be used for the detection and isolation of functional equivalents of SEQ ID NO:1, SEQ ID NO:3 or SEQ ID NO:5 from other plant species on the basis of sequence identities. In this context, part or all of the sequence of the SEQ ID NO:1, SEQ ID NO:3 or SEQ ID NO:5 in question is used as probe for screening in a genomic library or a cDNA library of the plant species in question or in a computer search for sequences of functional equivalents in electronic databases.

Preferred plant species are the undesired plants which have already been mentioned at the outset.

The invention furthermore comprises expression cassettes comprising
a) genetic control sequences in operable linkage with a nucleic acid sequence comprising
   i) a nucleic acid sequence with the nucleic acid sequence shown in SEQ ID NO:1, SEQ ID NO:3 or SEQ ID NO:5; or
   ii) a nucleic acid sequence which, on the basis of the degeneracy of the genetic code, can be derived from the amino acid sequence shown in SEQ ID NO:2, SEQ ID NO:4 or SEQ ID NO:6 by back translation; or
   iii) functional equivalents of the nucleic acid sequence SEQ ID NO:1 with at least 69% identity with SEQ ID NO:1; or functional equivalents of the nucleic acid sequence SEQ ID NO:3 with at least 69% identity with SEQ ID NO:3; or functional equivalents of the nucleic acid sequence SEQ ID NO:5 with at least 63% identity with SEQ ID NO:5; or
   iv) a nucleic acid sequence which, on the basis of the degeneracy of the genetic code, can be derived from the amino acid sequence of a functional equivalent of SEQ ID NO:2 with at least 73% identity with SEQ ID NO:2 by back translation; or a nucleic acid sequence which, on the basis of the degeneracy of the genetic code, can be derived from the amino acid sequence of a functional equivalent of SEQ ID NO:4 with at least 73% identity with SEQ ID NO:4 by back translation; or a nucleic acid sequence which, on the basis of the degeneracy of the genetic code, can be derived from the amino acid sequence of a functional equivalent of SEQ ID NO:6 with at least 72% identity with SEQ ID NO:6 by back translation; or
b) additional functional elements; or
c) a combination of a) and b);

and the use of expression cassettes comprising
a) genetic control sequences in operable linkage with a nucleic acid sequence according to the invention;
b) additional functional elements; or
c) a combination of a) and b);

for expressing an SSP which can be employed in in vitro assay systems. Both embodiments of the above-described expression cassettes are referred to below as expression cassettes according to the invention.

In accordance with a preferred embodiment, an expression cassette according to the invention comprises a promoter at the 5' end of the coding sequence and, at the 3' end, a transcription termination signal and, if appropriate, further genetic control sequences which are linked operably with the interposed nucleic acid sequence according to the invention.

The expression cassettes according to the invention are also understood as meaning analogs which can be brought about, for example by a combination of the individual nucleic acid sequences on a polynucleotide (multiple constructs), on a plurality of polynucleotides in a cell (cotransformation) or by sequential transformation.

Advantageous genetic control sequences of a) for expression cassettes according to the invention or for vectors comprising expression cassettes according to the invention are, for example, promoters such as the cos, tac, trp, tet, lpp, lac, lacIq, T7, T5, T3, gal, trc, ara, SP6, λ-PR or the λ-PL promoter, all of which can be used for expressing SSP in Gram-negative bacterial strains.

Further advantageous genetic control sequences are present, for example, in the promoters amy and SPO2, both of which can be used for expressing SSP in Gram-positive bacterial strains, and in the yeast or fungal promoters AUG1, GPD-1, PX6, TEF, CUP1, PGK, GAP1, TPI, PHO5, AOX1, GAL10/CYC1, CYC1, OliC, ADH, TDH, Kex2, MFa or NMT or combinations of the abovementioned promoters (Degryse et al., Yeast 1995 Jun. 15; 11(7):629-40; Romanos et al. Yeast 1992 June; 8(6):423-88; Benito et al. Eur. J. Plant Pathol. 104, 207-220 (1998); Cregg et al. Biotechnology (N Y) 1993 August; 11(8):905-10; Luo X., Gene 1995 Sep. 22; 163(1):127-31; Nacken et al., Gene 1996 Oct. 10; 175(1-2): 253-60; Turgeon et al., Mol Cell Biol 1987 September; 7(9):3297-305) or the transcription terminators NMT, Gcyl, TrpC, AOX1, nos, PGK or CYC1 (Degryse et al., Yeast 1995 Jun. 15; 11(7):629-40; Brunelli et al. Yeast Dec. 9, 1993 (12): 1309-18; Frisch et al., Plant Mol. Biol. 27 (2), 405-409 (1995); Scorer et al., Biotechnology (N.Y.) 12 (2), 181-184 (1994), GenBank Acc. Number Z46232; Zhao et al. GenBank Acc Number : AF049064; Punt et al., (1987) Gene 56 (1), 117-124), all of which can be used for expressing SSP in yeast strains.

Examples of genetic control sequences which are suitable for expression in insect cells are the polyhedrin promoter and the p10 promoter (Luckow, V. A. and Summers, M. D. (1988) Bio/Techn. 6, 47-55).

Advantageous genetic control sequences for expressing SSP in cell culture are, in addition to polyadenylation sequences such as, for example, from simian virus 40, eukaryotic promoters of viral origin such as, for example, promoters of the polyoma virus, adenovirus 2, cytomegalovirus or simian virus 40.

Further advantageous genetic control sequences for expressing SSP in plants are present in the plant promoters CaMV/35S [Franck et al., Cell 21(1980) 285-294], PRP1 [Ward et al., Plant. Mol. Biol. 22 (1993)], SSU, OCS, LEB4, USP, STLS1, B33, NOS; FBPaseP (WO 98/18940) or in the ubiquitin or phaseolin promoter; a promoter which is preferably used being, in particular, a plant promoter or a promoter derived from a plant virus. Especially preferred are promoters of viral origin, such as the promoter of the cauliflower mosaic virus 35S transcript (Franck et al., Cell 21 (1980), 285-294; Odell et al., Nature 313 (1985), 810-812). Further preferred constitutive promoters are, for example, the *Agrobacterium* nopaline synthase promoter, the TR dual promoter, the *Agrobacterium* OCS (octopine synthase) promoter, the ubiquitin promoter (Holtorf S et al., Plant Mol Biol 1995, 29:637-649), the promoters of the vacuolar ATPase subunits, or the promoter of a proline-rich protein from wheat (WO 91/13991).

The expression cassettes may also comprise, as genetic control sequence, a chemically inducible promoter, by means of which the expression of the exogenous gene in the plant can be controlled at a specific point in time. Such promoters, such as, for example, the PRP1 promoter (Ward et al., Plant. Mol. Biol. 22 (1993), 361-366), a salicylic-acid-inducible promoter (WO 95/19443), a benzenesulfonamide-inducible promoter (EP-A-0388186), a tetracyclin-inducible promoter (Gatz et al., (1992) Plant J. 2, 397404), an abscisic-acid-inducible promoter (EP-A 335528) or an ethanol- or cyclohexanone-inducible promoter (WO 93/21334) may also be used.

Furthermore, suitable promoters are those which confer tissue- or organ-specific expression in, for example, anthers, ovaries, influorescences and floral organs, leaves, stomata, trichomes, stems, vascular tissues, roots and seeds. Others which are suitable in addition to the abovementioned constitutive promoters are, in particular, those promoters which ensure leaf-specific expression. Promoters which must be mentioned are the potato cytosolic FBPase promoter (WO 97/05900), the RuBisCO (ribulose-1,5-bisphosphate carboxylase) SSU promoter (small subunit) or the ST-LSI promoter from potato (Stockhaus et al., EMBO J. 8 (1989), 2445-245). Promoters which are furthermore preferred are those which control expression in seeds and plant embryos. Examples of seed-specific promoters are the phaseolin promoter (U.S. Pat. No. 5,504,200, Bustos M M et al., Plant Cell. 1989;1(9):839-53), the promoter of the 25 albumin gene (Joseffson L G et al., J Biol Chem 1987, 262:12196-12201), the legumin promoter (Shirsat A et al., Mol Gen Genet. 1989;215(2):326-331), the USP (unknown seed protein promoter; Bäumlein H et al., Molecular & General Genetics 1991, 225(3):459-67), the promoter of the napin gene (Stalberg K, et al., L. Planta 1996, 199:515-519), the sucrose binding protein promoter (WO 00/26388) or the LeB4 promoter (Bäumlein H et al., Mol Gen Genet 1991, 225: 121-128; Fiedler, U. et al., Biotechnology (NY) (1995), 13 (10) 1090).

Further promoters which are suitable as genetic control sequences are, for example, specific promoters for tubers, storage roots or roots, such as, for example, the class I patatin promoter (B33), the potato cathepsin D inhibitor promoter, the starch synthase (GBSS1) promoter or the sporamin promoter, fruit-specific promoters such as, for example, the fruit-specific promoter from tomato (EP-A 409625), fruit-maturation-specific promoters such as, for example, the fruit-maturation-specific promoter from tomato (WO 94/21794), influoresence-specific promoters such as, for example, the phytoene synthase promoter (WO 92/16635) or the promoter of the P-rr gene (WO 98/22593), or plastid- or chromoplast-specific promoters such as, for example, the RNA polymerase promoter (WO 97/06250), or else the Glycine max phosphoribosyl pyrophosphate amidotransferase promoter (see also GenBank Accession No U87999), or another node-specific promoter as described in EP-A 249676 can be used advantageously.

Additional functional elements b) are understood as meaning by way of example but not by limitation reporter genes, replication origins, selection markers and what are known as affinity tags, in direct fusion with SSP or in fusion by means of a linker optionally comprising a protease cleavage site. Further suitable additional functional elements are sequences which ensure targeting into the apoplast, into plastids, into the vacuole, the mitochondrion, the peroxisome, the endoplasmic reticulum (ER), or, owing to the absence of such operative sequences, the remaining of the product in the compartment where it is formed, the cytosol (Kermode, Crit. Rev. Plant Sci. 15, 4 (1996), 285-423).

Also in accordance with the invention are vectors comprising at least one copy of the nucleic acid sequences according to the invention and/or the expression cassettes according to the invention.

In addition to plasmids, vectors are furthermore also understood as meaning all of the other known vectors with which the skilled worker is familiar, such as, for example, phages, viruses such as SV40, CMV, baculovirus, adenovirus, transposons, IS elements, phasmids, phagemids, cosmids, linear DNA or circular DNA. These vectors can replicate autonomously in the host organism or replicate chromosomally; chromosomal replication is preferred.

In a further embodiment of the vector, the nucleic acid construct according to the invention can advantageously also be introduced into the organisms in the form of a linear DNA and integrated into the genome of the host organism via heterologous or homologous recombination. This linear DNA may consist of a linearized plasmid or only of the nucleic acid construct as vector, or the nucleic acid sequences used.

Further procaryotic or eukaryotic expression systems are mentioned in chapters 16 and 17 in Sambrook et al., "Molecular Cloning: A Laboratory Manual." 2nd, ed., Cold Spring Harbor Laboratory, Cold Spring Harbor Laboratory Press, Cold Spring Harbor, N.Y., 1989. Further advantageous vectors are described in Hellens et al. (Trends in plant science, 5, 2000).

The expression cassette according to the invention and vectors derived therefrom can be used for transforming bacteria, cyanobacteria (for example of the genus *Synechocystis, Anabaena, Calothrix, Scytonema, Oscillatoria, Plectonema* and *Nostoc*), proteobacteria such as, for example, *Magnetococcus* sp. MC1, yeasts, filamentous fungi and algae and eukaryotic nonhuman cells (for example insect cells) with the aim of producing SSP recombinantly, the generation of a suitable expression cassette depending on the organism in which the gene is to be expressed.

In a further advantageous embodiment, the nucleic acid sequences used in the method according to the invention may also be introduced into an organism by themselves.

If, in addition to the nucleic acid sequences, further genes are to be introduced into the organism, they all can be introduced into the organism together in a single vector, or each individual gene can be introduced into the organism in in each case one vector, it being possible to introduce the different vectors simultaneously or in succession.

In this context, the introduction, into the organisms in question (transformation), of the nucleic acid(s) according to the invention, of the expression cassette or of the vector can be effected in principle by all methods with which the skilled worker is familiar.

In the case of microorganisms, the skilled worker will find suitable methods in the textbooks by Sambrook, J. et al. (1989) "Molecular cloning: A laboratory manual", Cold Spring Harbor Laboratory Press, by F. M. Ausubel et al. (1994) "Current protocols in molecular biology", John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Habor Laboratory Press or Guthrie et al. "Guide to Yeast Genetics and Molecular Biology", Methods in Enzymology, 1994, Academic Press. In the case of the transformation of filamentous fungi, methods of choice are firstly the generation of protoplasts and transformation with the aid of PEG (Wiebe et al. (1997) Mycol. Res. 101 (7): 971-877; Proctor et al. (1997) Microbiol. 143, 2538-2591) and secondly the transformation with the aid of *Agrobacterium tumefaciens* (de Groot et al. (1998) Nat. Biotech. 16, 839-842).

In the case of dicotyledonous plants, the methods which have been described for the transformation and regeneration of plants from plant tissues or plant cells can be exploited for transient or stable transformation. Suitable methods are the biolistic method or by protoplast transformation (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge), electroporation, the incubation of dry embryos in DNA containing solution, microinjection and the *agrobacterium*-mediated gene transfer. The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993)

128-143 and in Potrykus Annu. Rev. Plant Physiol. Plant Molec. Biol. 42 (1991) 205-225).

The transformation by means of agrobacteria, and the vectors to be used for the transformation, are known to the skilled worker and described extensively in the literature (Bevan et al., Nucl. Acids Res. 12 (1984) 8711. The intermediary vectors can be integrated into the agrobacterial Ti or Ri plasmid by means of homologous recombination owing to sequences which are homologous to sequences in the T-DNA. This plasmid additionally contains the vir region, which is required for the transfer of the T-DNA. Intermediary vectors are not capable of replicating in agrobacteria. The intermediary vector can be transferred to *Agrobacterium tumefaciens* by means of a helper plasmid (conjugation). Binary vectors are capable of replication both in *E.coli* and in agrobacteria. They contain a selection marker gene and a linker or polylinker which are framed by the right and left T-DNA border region. They can be transformed directly into the agrobacteria (Holsters et al. Mol. Gen. Genet. 163 (1978), 181-187), EP A 0 120 516; Hoekema, In: The Binary Plant Vector System Offsetdrukkerij Kanters B. V., Alblasserdam (1985), Chapter V; Fraley et al., Crit. Rev. Plant. Sci., 4: 1-46 and An et al. EMBO J. 4 (1985), 277-287).

The transformation of monocotyledonous plants by means of vectors based on *Agrobacterium* has also been described (Chan et al, Plant Mol. Biol. 22(1993), 491-506; Hiei et al, Plant J. 6 (1994) 271-282; Deng et al; Science in China 33 (1990), 28-34; Wilmink et al, Plant Cell Reports 11, (1992) 76-80; May et al; Biotechnology 13 (1995) 486-492; Conner and Domisse; Int. J. Plant Sci. 153 (1992) 550-555; Ritchie et al; Transgenic Res. (1993) 252-265). Alternative systems for the transformation of monocotyledonous plants are the transformation by means of the biolistic approach (Wan and Lemaux; Plant Physiol. 104 (1994), 37-48; Vasil et al; Biotechnology 11 (1992), 667-674; Ritala et al, Plant Mol. Biol 24, (1994) 317-325; Spencer et al, Theor. Appl. Genet. 79 (1990), 625-631) protoplast transformation, electroporation of partially permeabilized cells, and the introduction of DNA by means of glass fibers. In particular the transformation of maize has been described repeatedly in the literature (cf., for example, WO 95/06128; EP 0513849 A1; EP 0465875 A1; EP 0292435 A1; Fromm et al, Biotechnology 8 (1990), 833-844; Gordon-Kamm et al, Plant Cell 2 (1990), 603-618; Koziel et al, Biotechnology 11 (1993) 194-200; Moroc et al, Theor Applied Genetics 80 (190) 721-726).

The successful transformation of other cereal species has also already been described, for example in the case of barley (Wan and Lemaux, see above; Ritala et al, see above) and wheat (Nehra et al, Plant J. 5(1994) 285-297).

Agrobacteria which have been transformed with a vector according to the invention can likewise be used in a known manner for the transformation of plants, such as test plants such as *Arabidopsis* or crop plants like cereals, maize, oats, rye, barley, wheat, soya, rice, cotton, sugarbeet, canola, sunflower, flax, hemp, potato, tobacco, tomato, carrot, capsicum, oilseed rape, tapioca, cassava, arrowroot, Tagetes, alfalfa, lettuce and the various tree, nut and grapevine species, for example by bathing scarified leaves or leaf segments in an agrobacterial solution and subsequently growing them in suitable media.

The genetically modified plant cells can be regenerated via all methods with which the skilled worker is familiar. Such methods can be found in the abovementioned publications by S. D. Kung and R. Wu, Potrykus or Höfgen and Willmitzer.

The transgenic organisms generated by transformation with one of the above-described embodiments of an expression cassette comprising a nucleic acid sequence according to the invention or a vector comprising the abovementioned expression cassette, and the recombinant SSP which can be obtained from the transgenic organism by means of expression are subject matter of the present invention. The use of transgenic organisms comprising an expression cassette according to the invention, for example for providing recombinant proteins, and/or the use of these organisms in in vivo assay systems are likewise subject matter of the present invention.

Preferred organisms for the recombinant expression are not only bacteria, yeasts, mosses, algae and fungi, but also eukaryotic cell lines.

Preferred mosses are *Physcomitrella patens* or other mosses described in Kryptogamen [cryptogams], Vol. 2, Moose, Farne [mosses, ferns], 1991, Springer Verlag (ISBN 3540536515).

Preferred within the bacteria are those of the genus *Escherichia, Erwinia, Flavobacterium, Alcaligenes* or cyanobacteria, for example of the genus *Synechocystis, Anabaena, Calothrix, Scytonema, Oscillatoria, Plectonema* and *Nostoc,* especially preferably *Synechocystis* or *Anabena.*

Preferred yeasts are *Candida, Saccharomyces, Schizosaccheromyces, Hansenula* or *Pichia.*

Preferred fungi are *Aspergillus, Trichoderma, Ashbya, Neurospora, Fusarium, Beauveria, Mortierella, Saprolegnia, Pythium,* or other fungi described in Indian Chem Engr. Section B. Vol 37, No 1,2 (1995).

Preferred plants are selected in particular among monocotyledonous crop plants such as, for example, cereal species such as wheat, barley, sorghum and millet, rye, triticale, maize, rice or oats, and sugar cane. The transgenic plants according to the invention are, furthermore, selected in particular from among dicotyledonous crop plants such as, for example, *Brassicaceae* such as oilseed rape, cress, *arabidopsis,* cabbages or canola; Leguminosae such as soy bean, alfalfa, pea, beans or peanuts; Solanaceae such as potato, tobacco, tomato, eggplant or capsicum; Asteraceae such as sunflower, Tagetes, lettuce or *Calendula;* Cucurbitaceae such as melon, pumpkin/squash or zucchini, or linseed, cotton, hemp, flax, red pepper, carrot, sugarbeet, or various tree, nut and grapevine species.

In principle, transgenic animals such as, for example, *C. elegans,* are also suitable as host organisms.

Also preferred is the use of expression systems and vectors which are available to the public or commercially available.

Those which must be mentioned for use in *E. coli* bacteria are the typical advantageous commercially available fusion and expression vectors pGEX [Pharmacia Biotech Inc; Smith, D. B. and Johnson, K. S. (1988) Gene 67:31-40], pMAL (New England Biolabs, Beverly, M A) and pRIT5 (Pharmacia, Piscataway, N.J.), which contains glutathione S transferase (GST), maltose binding protein, or protein A, the pTrc vectors (Amann et al., (1988) Gene 69:301-315), "pKK233-2" by CLONTECH, Palo Alto, Calif., and the "pET" and the "pBAD" vector series from Stratagene, La Jolla.

Further advantageous vectors for use in yeast are pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), and pYES derivatives, pGAPZ derivatives, pPICZ derivatives and the vectors of the "*Pichia* Expression Kit" (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., p. 1-28, Cambridge University Press: Cambridge.

As an alternative, insect cell expression vectors may also be used advantageously, for example for expression in Sf9, Sf21 or Hi5 cells which are infected via recombinant baculoviruses. Examples of these are vectors of the pAc series (Smith et al. (1983) Mol. Cell Biol. 3:2156-2165) and of the pVL series (Lucklow and Summers (1989) Virology 170: 31-39). Others which may be mentioned are the baculovirus expression systems "MaxBac 2.0 Kit" and "Insect Select System" from Invitrogen, Carlsbad or the "BacPAK Baculovirus Expression System" from CLONTECH, Palo Alto, Calif. Insect cells are particularly suitable for overexpressing eukaryotic proteins since they effect posttranslational modifications of the proteins which are not possible in bacteria and yeasts. The skilled worker is familiar with the handling of cultured insect cells and with their infection for the purposes of expressing proteins, which can be carried out analogously to known methods (Luckow and Summers, Bio/Tech. 6, 1988, pp. 47-55; Glover and Hames (eds) in DNA Cloning 2, A practical Approach, Expression Systems, Second Edition, Oxford University Press, 1995, 205-244).

Plant cells or algal cells are others which can be used advantageously for expressing genes. Examples of plant expression vectors can be found as mentioned above in Bekker, D., et al. (1992) "New plant binary vectors with selectable markers located proximal to the left border", Plant Mol. Biol. 20: 1195-1197 or in Bevan, M. W. (1984) "Binary *Agrobacterium* vectors for plant transformation", Nucl. Acid. Res. 12: 8711-8721.

Moreover, the nucleic acid sequences according to the invention can be expressed in mammalian cells. Examples suitable for expression vectors are pCDM8 and pMT2PC, which are mentioned in: Seed, B. (1987) Nature 329:840 or Kaufman et al. (1987) EMBO J. 6:187-195). Promoters to be used by preference in this context are of viral origin such as, for example, promoters of polyoma, adenovirus 2, cytomegalovirus or simian virus 40. Further prokaryotic and eukaryotic expression systems are mentioned in chapters 16 and 17 in Sambrook et al., Molecular Cloning: A Laboratory Manual. 2nd, ed., Cold Spring Harbor Laboratory, Cold Spring Harbor Laboratory Press, Cold Spring Harbor, N.Y., 1989. Further advantageous vectors are described in Hellens et al. (Trends in plant science, 5, 2000).

All of the abovementioned embodiments of the transgenic organisms come under the term "transgenic organism according to the invention".

The present invention furthermore relates to the use of SSP in a method for identifying herbicidally active test compounds.

Preferably, the method according to the invention for identifying herbicidally active compounds comprises the following steps:
i. bringing SSP into contact with one or more test compounds under conditions which permit binding of the test compound(s) to SSP; and
ii. detecting whether the test compound binds to the SSP of i); or
iii. detecting whether the test compound reduces or blocks the activity of the SSP of i); or
iv. detecting whether the test compound reduces or blocks the transcription, translation or expression of SSP.

Detection in accordance with step (ii) of the above method can be effected using techniques which identify the interaction between protein and ligand. In this context, either the test compound or the enzyme may contain the detectable label such as, for example, a fluorescent label, a radioisotope label, a chemiluminescent label or an enzyme label. Examples of enzyme labels are horseradish peroxidase, alkaline phosphatase or luciferase. The detection which follows depends on the label and is known to the skilled worker.

In this context; five preferred embodiments which are also suitable for high-throughput methods (HTS) in connection with the present invention must be mentioned in particular:
1. The average diffusion rate of a fluorescent molecule as a function of the mass can be determined in a small sample volume via fluorescence correlation spectroscopy (FCS) (Proc. Natl. Acad. Sci. USA (1994) 11753-11575). FCS can be employed for determining protein/ligand interactions by measuring the change in the mass, or the changed diffusion rate which this entails, of a test compound when binding to SSP. A method according to the invention can be designed directly for measuring the binding of a test compound labeled with a fluorescence molecule. As an alternative, the method according to the invention can be designed in such a way that a chemical reference compound which is labeled with a fluorescent molecule is displaced by further test compounds ("displacement assay"). The compounds identified thus may be suitable as inhibitors.
2. Fluorescence polarization exploits the characteristic of a quiescent fluorophore which is excited with polarized light to likewise emit polarized light. If, however, the fluorophore is allowed to rotate during the excited state, the polarization of the fluorescent light which is emitted is more or less lost. Under otherwise identical conditions (for example temperature, viscosity, solvent), rotation is a function of molecule size, whereby findings regarding the size of the fluorophore-bound residue can be obtained via the reading (Methods in Enzymology 246 (1995), pp. 283-300). A method according to the invention can be designed directly for measuring the binding, to SSP, of a test compound labeled with a fluroescent molecule. As an alternative, the method according to the invention may also take the form of the "displacement assay" described under 1. The compounds identified thus may be suitable as inhibitors.
3. "Fluorescent resonant energy tranfer" (FRET) is based on irradiation-free energy transfer between two spatially adjacent fluroescent molecules under suitable conditions. A prerequisite is that the emission spectrum of the donor molecule overlaps with the excitation spectrum of the acceptor molecule. Using the fluorescent label of SSP and the on binding test compound, the binding can be measured by means of FRET (Cytometry 34, 1998, pp. 159-179). As an alternative, the method according to the invention may also take the form of the "displacement assay" described under 1. An especially suitable embodiment of FRET technology is "Homogenous Time Resolved Fluorescence" (HTRF) as can be obtained from Packard BioScience. The compounds identified thus may be suitable as inhibitors.
4. Surface-enhanced laser desorption/ionization (SELDI) in combination with a "Time of Flight" mass spectrometer (MALDI-TOF) makes possible the rapid analysis of molecules on a support and can be used for analyzing protein-ligand interactions (Worral et al., (1998) Anal. Biochem. 70:750-756). In a preferred embodiment, SSP is immobilized on a suitable support and incubated with the test compound. After one or more suitable washing steps, the test compound molecules which are additionally bound to SSP can be detected by means of the abovementioned methodology and test compounds bound to SSP can be selected thus. The compounds which are identified thus may be suitable as inhibitors.

5. The measurement of surface plasmon resonance is based on the change in the refractive index at a surface when a test compound binds to a protein which is immobilized to said surface. Since the change in the refractive index is identical for virtually all proteins and polypeptides for a defined change in the mass concentration at the surface, this method can be applied to any protein in principle (Lindberg et al. Sensor Actuators 4 (1983) 299-304; Malmquist Nature 361 (1993) 186-187). The measurement can be carried out for example with the automatic analyzer based on surface plasmon resonance which is available from Biacore (Freiburg) at a throughput of, currently, up to 384 samples per day. A method according to the invention can be designed directly for measuring the binding of a test compound to SSP. As an alternative, the method according to the invention may also take the form of the "displacement assay" described under 1. The compounds identified thus may be suitable as inhibitors.

All of the substances identified via the abovementioned method can subsequently be checked for their herbicidal action in another embodiment of the method according to the invention.

Furthermore, there exists the possibility of detecting further candidates for herbicidal active ingredients by means of molecular modeling via elucidation of the three-dimensional structure of SSP by X-ray structure analysis. The preparation of protein crystals required for X-ray structure analysis, and the relevant measurements and subsequent evaluations of these measurements, the detection of a binding site in the protein, and the prediction of potential inhibitor structures, are known to the skilled worker. In principle, optimization of the compounds identified by the abovementioned method is also possible via molecular modeling.

A preferred embodiment of the method according to the invention, which is based on steps i) and ii), consists in
i. expressing an SSP in a transgenic organism according to the invention, or growing an organism which naturally contains an SSP;
ii. bringing the SSP of step i) in the cell digest of the transgenic or nontransgenic organism, in partially purified form or in homogeneously purified form, into contact with a test compound; and
iii. selecting a compound which reduces or blocks the SSP activity, the activity of the SSP incubated with the test compound being determined with the activity of an SSP not incubated with a test compound.

The SSP-comprising solution may consist of the lysate of the original organism or of the transgenic organism which has been transformed with an expression casette according to the invention. If appropriate, the SSP can be purified partially or fully via customary methods. A general overview over current protein purification techniques is described, for example, in Ausubel, F. M. et al., Current Protocols in Molecular Biology, Greene Publishing Assoc. and Wiley-Interscience (1994); ISBN 0-87969-309-6. If SSP is obtained recombinantly, the protein, which is fused to an affinity tag, can be purified via affinity chromatography as is known to the skilled worker.

The SSP which is required for in vitro methods can thus be isolated either by means of heterologous expression from a transgenic organism according to the invention or from an organism with SSP activity, preferably from an undesired plant, the term "undesired plant" being understood as meaning the species mentioned at the outset.

To identify herbicidal compounds, the SSP is incubated with a test compound. After a reaction time, the activity of the SSP incubated with a test compound is determined in comparison with the activity of an SSP which is not incubated with a test compound. If the SSP is inhibited, a significant decrease in activity is observed in comparison with the activity of the uninhibited polypeptide according to the invention, the result being a reduction of at least 10%, advantageously at least 20%, preferably at least 30%, especially preferably at least 50%, up to 100% reduction (blocking). Preferred is an inhibition of at least 50% at test compound concentrations of $10^{-4}$ M, preferably at $10^5$ M, especially preferably at $10^{-6}$ M, based on enzyme concentration in the micromolar range.

The enzymatic activity of SSP can be determined for example by an activity assay in which the increase in the product, the decrease in the substrate (or starting material) or a combination of at least two of the abovementioned parameters are determined as a function of a defined period.

Examples of suitable substrates are, for example, sucrose-6-phosphate or nitrophenyl compounds such as, for example, p-nitrophenyl phosphate, preferably sucrose-6-phosphate, and examples of suitable cofactors are divalent metals such as magnesium or manganese, preferably magnesium. If appropriate, derivatives of the abovementioned compounds which contain a detectable label such as, for example, a fluorescent label, a radioisotope label or a chemiluminescent label, may also be used.

The amounts of substrate to be employed in the activity assay can range between 0.5-10 mM and the amounts of cofactor can range between 0.1-5 mM, based on 1-100 μg/ml enzyme.

The activity can be determined for example in analogy to the method described by Echeverria and Salerno (1994; Plant Sci 96, 15) or by the method described by Whitaker (1984) Phytochemistry 23, 2429).

In an especially preferred embodiment, the conversion of a substrate is determined via quantifying the phosphate formed during the reaction by means of ascorbate/ammonium molybdate reagent (Ames (1966), Methods Enzymol. 8, 115), following a method of Lunn et al. (2000, Procl. Natl. Acad. Sci. USA 97: 12914). However, modifications of Ames' method described for detecting phosphate may also be used, for example the method described by Chifflet et al. (1988) Analytical Biochemistry 168: 1), which is particularly suitable for unstable organic phosphates and in the presence of high protein concentrations, the method described by Lanzetta et al. (1979, Analytical Biochemistry 100: 95), which encompasses a method for detecting phosphate in the nanomole range, in which method the resulting dye complex is stabilized in a particular fashion. Others which can be used for detection are commercially available kits, for example from Merck (Phosphate assay (PMB) AM catalog number 1.11139.0001)).

In a further preferred embodiment, the activity can be determined on the basis of the sucrose liberated from sucrose-6-P. Suitable for this purpose are, for example, optical-enzymatic methods, for example those described by Sonnewald (1992, Plant Journal 2: 571) or chromatographic methods using HPLC (Börnke et al. 2001, J Bacteriol 183: 2425). Moreover, methods for chemically detecting the sucrose formed can also be found by the skilled worker in the literature.

A preferred embodiment of the method according to the invention which is based on steps i) and iii) consists of the following steps:
i) generation of a transgenic organism according to the invention;
ii) applying a test compound to the transgenic organism of i) and to a nontransgenic organism of the same genotype;
iii) determining the growth or the viability of the transgenic and nontransgenic organisms after application of the test compound; and
iv) selection of test compounds that bring about a reduced growth or reduced viability of the nontransgenic organism in comparison with the growth of the transgenic organism.

In this method, the polypeptide with the biological activity of an SSP is overexpressed in the transgenic organism of i). The transgenic organism thus shows an increased SSP activity in comparison with a nontransgenic organism, increased SSP activity of the transgenic organism meaning an activity which is increased by at least 10%, preferably by at least 25%, especially preferably by at least 40%, very especially preferably by at least 50% in comparison with the nontransgenic organism of the same genus.

In this context, the difference in growth in step iv) for the selection of a herbicidally active inhibitor amounts to at least 10%, by preference 20%, preferably 30%, especially preferably 40% and very especially preferably 50%.

The transgenic organism in this context is a plant, an alga, a cyanobacterium, for example of the genus *Synechocystis, Anabaena, Calothrix, Scytonema, Oscillatoria, Plectonema* and *Nostoc*, or a proteobacterium such as, for example, *Magnetococcus* sp., MC1, preferably plants which can readily be transformed by means of customary techniques, such as *Arabidopsis thaliana, Solanum tuberosum, Nicotiana tabacum*, cyanobacteria which can be transformed readily, such as, for example, *Synechocystis*, into which the sequence encoding a polypeptide according to the invention has been incorporated via transformation. These transgenic organisms thus display increased tolerance to compounds which inhibit the polypeptide according to the invention. "Knock-out" mutants, in which the analogous SSP gene which is present in this organism has been eliminated in a directed fashion may also be used for this purpose.

However, the abovementioned embodiment of the method according to the invention may also be used for identifying growth-regulatory substances. In this context, the transgenic organism employed is a plant. The method for identifying growth-regulatory substances thus encompasses the following steps:
i) generation of a transgenic plant comprising a nucleic acid sequence according to the invention;
ii) applying a test substance to the transgenic plant of i) and to a nontransgenic plant of the same cultivar;
iii) determining the growth or the viability of the transgenic plant and the nontransgenic plants after application of the test substance; and
iv) selection of test substances which bring about a modified growth of the nontransgenic plant in comparison with the growth of the transgenic plant.

In this method, the polypeptide with the biological activity of an SSP is overexpressed in the transgenic plant of i). The transgenic plant thus shows an increased SSP activity in comparison with a nontransgenic plant, increased SSP activity of the transgenic plant meaning an activity which is increased by at least 10%, preferably by at least 25%, especially preferably by at least 40%, very especially preferably by at least 50% in comparison with a nontransgenic plant of the same genus.

In this context, test compounds are selected in step iv) which bring about a modified growth of the nontransgenic organism in comparison with the growth of the transgenic organism. Modified growth in this context is understood as meaning an inhibition of the vegetative growth of the plants, which may be manifested in particular in reduced longitudinal growth. Accordingly, the treated plants show stunted growth; moreover, the leaves are darker. In addition, modified growth is also understood as meaning a change in the course of maturation over time, an inhibition or promotion of lateral branched growth of the plants, shortened or extended developmental stages, increased standing ability, the growth of larger amounts of buds, flowers, leaves, fruits, seed kernels, roots and tubers, an increased sugar content in plants such as sugar beet, sugar cane and citrus fruit, an increased protein content in plants such as cereals or soybean, or stimulation of the latex flow in rubber trees. The skilled worker is familiar with the detection of such modified growth.

It is also possible, in the method according to the invention, to employ a plurality of test compounds in a method according to the invention. If a group of test compounds affect the target, then it is either possible directly to isolate the individual test compounds or to divide the group of test compounds into a variety of subgroups, for example when it consists of a multiplicity of different components, in order to reduce the number of the different test compounds in the method according to the invention. The method according to the invention is then repeated with the individual test compound or the relevant subgroup of test compounds. Depending on the complexity of the sample, the above-described steps can be carried out repeatedly, preferably until the subgroup identified in accordance with the method according to the invention only comprises a small number of test compounds, or indeed just one test compound.

All of the methods for identifying herbicidal inhibitors are hereinbelow termed as "methods according to the invention".

All of the compounds which have been identified by the methods according to the invention can subsequently be tested in vivo for their herbicidal action. One possibility of testing the compounds for herbicidal action is to use duckweed, Lemna minor, in microtiter plates. Parameters which can be measured are modifications in the chlorophyll content and the photosynthesis rate. It is also possible to apply the compound directly to undesired plants, it being possible to identify the herbicidal action for example via restricted growth.

The method according to the invention can advantageously also be carried out in high-throughput methods, also known as HTS methods, which makes possible the parallel testing of a multiplicity of different compounds.

The use of supports which contain one or more of the nucleic acid molecules according to the invention, one or more of the vectors comprising the nucleic acid sequence according to the invention, one or more transgenic organisms comprising at least one of the nucleic acid sequences according to the invention, or one or more (poly)peptides encoded via the nucleic acid sequences according to the invention lends itself to carrying out an HTS method in practice. The support used can be solid or liquid, it is preferably solid and especially preferably a microtiter plate. The abovementioned supports are also subject matter of the present invention. In accordance with the most widely used technique, 96-well, 384-well and 1536-well microtiter plates which, as a rule, can comprise volumes of 200 µl, are used. Besides the microtiter plates, the other components of an HTS system which match the corresponding microtiter plates, such as a large number of instruments, materials, automatic pipetting devices, robots, automated plate readers and plate washers, are commercially available.

In addition to the HTS methods, based on microtiter plates, what are known as "free-format assays" or assay systems where no physical barriers exist between the samples can be used, such as, for example, in Jayaickreme et al., Proc. Natl. Acad. Sci U.S.A. 19 (1994) 161418; Chelsky, "Strategies for Screening Combinatorial Libaries", First Annual Conference of The Society for Biomolecular Screening in Philadelphia, Pa. (Nov. 710, 1995); Salmon et al., Molecular Diversity 2 (1996), 5763 and U.S. Pat. No. 5,976,813.

The invention furthermore relates to herbicidally active compounds identified by the method according to the invention. These compounds are hereinbelow referred to as "selected compounds". They have a molecular weight of less than 1000 g/mol, advantageously less than 500 g/mol, preferably less than 400 g/mol, especially preferably less than 300 g/mol. Herbicidally active compounds have a Ki value of less than 1 mM, preferably less than 1 µM, especially preferably less than 0.1 µM, very especially preferably less than 0.01 µM.

Naturally, the selected compounds may also be present in the form of their agriculturally useful salts. Agriculturally useful salts which are suitable are mainly the salts of those cations, or the acid addition salts of those acids, whose cations, or anions, respectively, do not adversely affect the herbicidal action of the herbicidally active compounds identified by the methods according to the invention.

If the selected compounds contain asymmetrically substituted α-carbon atoms, they may furthermore either be present in the form of racemates, enantiomer mixtures, pure enantiomers or, if they have chiral substituents, also in the form of diastereomer mixtures.

The selected compounds may take the form of chemically synthesized substances or substances produced by microorganisms; they can be found, for example, in cell extracts of, for example, plants, animals or microorganisms. The reaction mixture can be a cell-free extract or comprise a cell or cell culture. Suitable methods are known to the skilled worker and are described generally for example in Alberts, Molecular Biology the cell, $3^{rd}$ Edition (1994), for example chapter 17. The selected compounds may also originate from extensive substance libraries.

Candidate test compounds can be expression libraries such as, for example, cDNA expression libraries, peptides, proteins, nucleic acids, antibodies, small organic substances, hormones, PNAs or the like (Milner, Nature Medicin 1 (1995), 879-880; Hupp, Cell. 83 (1995), 237-245; Gibbs, Cell. 79 (1994), 193-198 and references cited therein).

The selected compounds can be used for controlling undesired vegetation, if appropriate also for the defoliation of, for example, potatoes, or the desiccation of, for example, cotton, and as growth regulators. Herbicidal compositions comprising the selected compounds afford very good control of vegetation on noncrop areas. In crops such as wheat, rice, maize, soybean and cotton, they act on broad-leaved weeds and grass weeds without inflicting any significant damage on the crop plants. This effect is observed in particular at low application rates. The selected compounds can be used for controlling the harmful plants which have already been mentioned above.

Depending on the application method in question, selected compounds, or herbicidal compositions comprising them, can advantageously also be employed in a further number of crop plants for eliminating undesired plants. Examples of suitable crops are:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

In addition, the selected compounds can also be used in crops which tolerate the action of herbicides owing to breeding, including recombinant methods. The generation of such crops is described hereinbelow.

The invention furthermore relates to a method of preparing the herbicidal composition which has already been mentioned above, which comprises formulating selected compounds with suitable adjuvants to give crop protection products.

The selected-compounds can be formulated for example in the form of directly sprayable aqueous solutions, powders, suspensions, also highly concentrated aqueous, oily or other suspensions or suspoemulsions or dispersions, emulsifiable concentrates, emulsions, oil dispersions, pastes, dusts, materials for spreading or granules and be used by means of spraying, atomizing, dusting, spreading or pouring. The use forms depend on the intended use and on the nature of the selected compounds; in any case, they should guarantee the finest possible distribution of the selected compounds. The herbicidal compositions comprise a herbicidally active amount of at least one selected compound and adjuvants conventionally used in the formulation of herbicidal compositions.

For the preparation of emulsions, pastes or aqueous or oily formulations and dispersible concentrates (DC), the selected compounds can be dissolved or dispersed in an oil or solvent, it being possible to add further formulation auxiliaries for homogenization purposes. However, it is also possible to prepare liquid or solid concentrates from selected compounds, if appropriate solvents or oil and, optionally, further adjuvants, and such concentrates are suitable for dilution with water. The following may be mentioned: emulsifiable concentrates (EC, EW), suspensions (SC), soluble concentrates (SL), dispersible concentrates (DC), pastes, pills, wettable powders or granules, it being possible for the solid formulations either to be soluble or dispersible (wettable) in water. In addition, suitable powders or granules or tablets can additionally be provided with a solid coating which prevents abrasion or premature release of the active ingredient.

In principle, the term "adjuvant" is understood as meaning the following classes of compounds: antifoams, thickeners, wetters, stickers, dispersants, emulsifiers, bactericides and/or thixotropic agents. The skilled worker is familiar with the meaning of the abovementioned agents.

SLs, EWs and ECs can be prepared by simply mixing the constituents in question; powders can be prepared by mixing or grinding in specific types of mills (for example hammer mills). DC, SCs and SEs are usually prepared by wet milling, it being possible to prepare an SE from an SC by adding an organic phase which may comprise further adjuvants or selected compounds. The preparation is known. Powders, materials for spreading and dusts can advantageously be prepared by mixing or concomitantly grinding the active substances together with a solid carrier. Granules, for example coated granules, impregnated granules and homogeneous granules, can be prepared by grinding the selected compounds to solid carriers. The skilled worker is familiar with further details regarding their preparation, which are provided for example in the-following publications: U.S. Pat. No. 3,060,084, EP-A 707445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Federal Republic of Germany), 2001.

The skilled worker is familiar with a multiplicity of inert liquid and/or solid carriers which are suitable for the formulations according to the invention, such as, for example, liquid additives such as mineral oil fractions of medium to high boiling point such as kerosene or diesel oil, furthermore coal tar oils and oils of vegetable or animal origin, or aliphatic, cyclic and aromatic hydrocarbons, for example paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone or strongly polar solvents, for example amines such as N-methylpyrrolidone or water.

Examples of solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders and other solid carriers.

The skilled worker is familiar with a multiplicity of surface-active substances (surfactants) which are suitable for the formulations according to the invention such as, for example, alkali metal salts, alkaline earth metal salts or ammonium salts of aromatic sulfonic acids, for example ligninsulfonic acid, phenolsulfonic acid, naphthalenesulfonic acid and dibutylnaphthalenesulfonic acid, and of fatty acids, of alkyl- and alkylarylsulfonates, of alkyl sulfates, lauryl ether sulfates and fatty alcohol sulfates, and also salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

The herbicidal compositions, or the selected compounds, can be applied pre- or post-emergence. If the selected compounds are less well tolerated by certain crop plants, application techniques may be used in which the selected compounds are sprayed, with the aid of the spraying apparatus, in such a way that they come into as little contact, if any, with the leaves of the sensitive crop plants while the selected compounds reach the leaves of undesired plants which grow underneath, or the bare soil surface (post-directed, lay-by).

Depending on the intended aim of the control measures, the season, the target plants and the growth stage, the application rates of selected compounds amount to 0.001 to 3.0, preferably 0.01 to 1.0 kg/ha.

Providing the herbicidal target furthermore enables a method for identifying a protein with the biological activity of an SSP which is not inhibited, or inhibited to a limited extent only, by a herbicide which has SSP as its site of action, for example the herbicidally active compounds which have been selected. In the following text, such a protein which differs in this way from SSP is referred to as SSP variant, which is encoded by a nucleic acid sequence which i) encodes a polypeptide with the biological activity of a sucrose-6-phosphate phosphatase which polypeptide is not inhibited by herbicidally active substances which inhibit SSP and which are identified by the abovementioned methods;

ii) is encoded by a functional equivalent of the nucleic acid sequence SEQ ID NO:1 with at least 55% identity with SEQ ID NO:1; or functional equivalents of the nucleic acid sequence SEQ ID NO:3 with at least 55% identity with SEQ ID NO:3; or functional equivalents of the nucleic acid sequence SEQ ID NO:5 with at least 51% identity with SEQ ID NO:5.

In a preferred embodiment, the abovementioned method for generating nucleic acid sequences encoding SSP variants of nucleic acid sequences comprises the following steps:

a) expressing the protein encoded by the abovementioned nucleic acids in a heterologous system or a cell-free system;

b) random or site-directed mutagenesis of the protein by modification of the nucleic acid;

c) measuring the interaction of the modified gene product the herbicide;

d) identifying derivatives of the protein which show less interaction;

e) assaying the biological activity of the protein after application of the herbicide;

f) selecting the nucleic acid sequences which have a modified biological activity against the herbicide.

The functional equivalents of SEQ ID NO:1 in accordance with ii) have at least 55%, 56%, 57%, 58%, 59%, 60%, 61%, 62%, 63%, 64%, 65%, 66%, 67%, 68%, by preference at least 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 90%, 91%, 92%, 93%, especially preferably at least 94%, 95%, 96%, 97%, 98%, 99% homology with SEQ ID No:1.

The functional equivalents of SEQ ID NO:3 in accordance with ii) have at least 55%, 56%, 57%, 58%, 59%, 60%, 61%, 62%, 63%, 64%, 65%, 66%, 67%, 68%, by preference at least 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 90%, 91%, 92%, 93%, especially preferably at least 94%, 95%, 96%, 97%, 98%, 99% homology with SEQ ID No:3.

The functional equivalents of SEQ ID NO:5 in accordance with ii) have at least 51%, 52%, 53%, 54%, 55%, 56%, 57%, 58%, 59%, 60%, 61%, 62%, by preference at least 63%, 64%, 65%, 66%, 67%, 68%, 69%, 70%, 71%, 72%, 73%, 74%, by preference at least 75%, 76%, 77%, 78%, 79%, 80%, 81%, 82%, 83%, preferably at least 84%, 85%, 86%, 87%, 88%, 89%, 90%, 91%, 92%, 93%, especially preferably at least 94%, 95%, 96%, 97%, 98%, 99% homology with SEQ ID No:5.

The sequences selected by the above-described method are advantageously introduced into an organism. The invention therefore furthermore relates to an organism generated by this method. The organism is preferably a plant, especially preferably one of the above-defined crop plants.

Thereafter, intact plants are regenerated and the resistance to the selected compound is verified in intact plants.

Modified proteins and/or nucleic acids which are capable of conferring, in plants, resistance to the selected compounds can also be generated from the abovementioned nucleic acid sequences via what is known as "site-directed mutagenesis"; this mutagenesis allows for example highly targeted improvement or modification of the stability and/or activity of the target protein or the characteristics such as binding and effect of the abovementioned inhibitors according to the invention.

An example of a "site-directed mutagenesis" method in plants hich can be used advantageously is the method described by Zhu et al. (Nature Biotech., Vol. 18, May 2000: 555-558).

Moreover, modifications can be achieved via the PCR method described by Spee et al. (Nucleic Acids Research, Vol. 21, No. 3, 1993: 777-78) using dITP for achieving random mutagenesis, or by the method which has been improved further by Rellos et al. (Protein Expr. Purif., 5, 1994: 270-277).

A further possibility for generating these modified proteins and/or nucleic acids is an in vitro recombination technique for molecular evolution which has been described by Stemmer et al. (Proc. Natl. Acad. Sci. USA, Vol. 91, 1994: 10747-10751) or the combination of the PCR and recombination method which has been described by Moore et al. (Nature Biotechnology Vol. 14, 1996: 458-467).

A further way of mutagenizing proteins is described by Greener et al. in Methods in Molecular Biology (Vol. 57, 1996: 375-385). A method for modifying proteins using the microorganism *E. coli* XL-1 Red is described in EP-A-0 909 821. Upon replication, this microorganism generates mutations in the nucleic acids introduced, and thus leads to a modification of the genetic information. Advantageous nucleic acids and the proteins encoded by them can be identified readily via isolation of the modified nucleic acids or the modified proteins and testing for resistance. These nucleic acids can then lead to the manifestation of resistance after introduction into plants and thus lead to resistance to the herbicides.

Further mutagenesis and selection methods are, for example, methods such as the in vivo mutagenesis of seeds or pollen and the selection of resistant alleles in the presence of the inhibitors according to the invention, followed by genetic and molecular identification of the modified resistant alleles; furthermore, the mutagenesis and selection of resistances in cell culture by propagating the culture in the presence of successively increasing concentrations of the inhibitors according to the invention. Here, it is possible to exploit the increase in the spontaneous mutation rate brought about by chemico-physical mutagenic treatment. As described above, it is also possible to isolate modified genes with the aid of microorganisms which have an endogenous or recombinant activity of the proteins encoded by the nucleic acids used in the method used according to the invention and which are sensitive to the inhibitors identified in accordance with the invention. Growing the microorganisms on media with increasing concentrations of inhibitors according to the invention permits the selection and evolution of resistant variants of the targets according to the invention. The mutation frequency, in turn, can be increased by mutagenic treatments.

Methods for the specific modifications of nucleic acids are also available (Zhu et al. Proc. Natl. Acad. Sci. USA, Vol. 96, 8768-8773 and Beetham et al., Proc. Natl. Acad. Sci. USA, Vol 96, 8774-8778). These methods allow the replacement, in the proteins, of those amino acids which are important for the binding of inhibitors by functionally analogous amino acids which, however, prevent the binding of the inhibitor.

The invention therefore furthermore relates to a method for generating nucleic acid sequences which encode gene products which have a modified biological activity, the biological activity having been modified in such a way that an increased activity is present. An increased activity is understood as meaning an activity which is at least 10%, preferably at least 30%, especially preferably at least 50%, very especially preferably at least 100% higher than that of the starting organism, or the starting gene product. Moreover, the biological activity can have been modified in such a way that the substances and/or compositions according to the invention no longer bind, or no longer correctly bind, to the nucleic acid sequences and/or the gene products encoded by them. For the purposes of the invention, "no longer" or "no longer correctly" means that the substances bind at least 30%, preferably at least 50%, particularly preferably at least 70%, very particularly preferably at least 80% less or not at all to the modified nucleic acids and/or gene products in comparison with the starting gene product or the starting nucleic acids.

Yet a further aspect of the invention therefore relates to a transgenic plant which has been transformed with a nucleic acid sequence which encodes a gene product with a modified biological activity, or with a nucleic acid sequence encoding an SSP variant. Transformation methods are known to the skilled worker, and examples are detailed further above.

Genetically modified transgenic plants which are resistant to substances found by the methods according to the invention and/or to compositions comprising these substances can also be generated by transformation, followed by overexpression of a nucleic acid sequence according to the invention. The invention therefore furthermore relates to a method for the generation of transgenic plants which are resistant to substances which have been found by a method according to the invention, wherein nucleic acids encoding an SSP variant are overexpressed in these plants. A similar method is described for example in Lermantova et al., Plant Physiol., 122, 2000: 75-83.

The above-described methods according to the invention for the generation of resistant plants make possible the development of novel herbicides which have as comprehensive and plant-species-independent activity as possible (also known as nonselective herbicides) in combination with the development of crop plants which are resistant to the non-selective herbicide. Crop plants which are resistant to non-selective herbicides have already been described on several occasions. In this context, we differentiate between a plurality of principles for obtaining a resistance:
a) Generation of resistance in a plant via mutation methods or recombinant methods, by overproducing to a substantial degree the protein which acts as target for the herbicide and by retaining the function exerted by this protein in the cell even after application of the herbicide owing to the large excess of the protein which acts as target for the herbicide.
b) Modification of the plant in such a way that a modified version of the protein which acts as target for the herbicide is introduced and that the function of the newly introduced modified protein is not adversely affected by the herbicide.
c) Modification of the plant in such a way that a novel protein/a novel RNA is introduced, wherein the chemical structure of the protein or of the nucleic acid such as the RNA or the DNA, which structure is responsible for the herbicidal activity of the low-molecular-weight substance, is modified in such a way that, owing to the modified structure, a herbicidal activity can no longer be exerted, i.e. the interaction of the herbicide with the target can no longer take place.
d) Replacement of the function of the target by a novel gene which is introduced into the plant, thus creating what is known as an alternative pathway.
e) The function of the target is taken over by another gene which is present in the plant, or its gene product.

The skilled worker is familiar with alternative methods for identifying the homologous nucleic acids, for example in other plants with similar sequences such as, for example, using transposons. The invention therefore also relates to the use of alternative insertion mutagenesis methods for the insertion of foreign nucleic acids into the nucleic acid sequences SEQ ID NO:1, SEQ ID NO:3 and SEQ ID NO:5 into sequences derived from these sequences on the basis of the genetic code, and/or their derivatives in other plants.

The transgenic plants are generated with one of the above-described embodiments of the expression cassette according to the invention by customary transformation methods, which have likewise been described above.

The expression efficacy of the recombinantly expressed SSP can be determined for example in vitro by shoot meristem propagation or by a germination test. Moreover, an expression of the SSP gene, which has been modified with regard to type and level, and its effect on the resistance to SSP inhibitors, can be tested on test plants in greenhouse experiments.

DETAILED DESCRIPTION OF EMBODIMENTS OF THE INVENTION

The invention is illustrated in greater detail by the examples which follow, which are not to be considered as limiting.

General DNA manipulation and cloning methods

Cloning methods such as, for example, restriction cleavages, agarose gel electrophoresis, purification of DNA fragments, transfer of nucleic acids to nitrocellulose and nylon membranes, linking DNA fragments, transformation of *Escherichia coli* cells, growing bacteria and sequence analysis of recombinant DNA were carried out as described by Sambrook et al. (1989) (Cold Spring Harbor Laboratory Press: ISBN 0-87969-309-6) and Ausubel, F. M. et al., Current Protocols in Molecular Biology, Greene Publishing Assoc. and Wiley-Interscience (1994); ISBN 0-87969-309-6.

Molecular-biological standard methods for plants and plant transformation methods are described in Schultz et al., Plant Molecular Biology Manual, Kluwer Academic Publishers (1998), Reither et al., Methods in *Arabidopsis* Research, World scientific press (1992) and *Arabidopsis*: A Laboratory Manual (2001), ISBN 0-87969-573-0.

The bacterial strains used hereinbelow (*E. coli* DH5α, XL-1 blue, BL21DE(3), JM 109) were obtained from Stratagene, BRL Gibco or Invitrogen, Carlsberg, Calif. The vectors used for cloning were pCR-Blunt (Invitrogen) and pUC 18 from Amersham Pharmacia (Freiburg), pBinAR (Höfgen and Willmitzer, Plant Science 66, 1990, 221-230), pCR and pQE-9 (Qiagen, Hilden).

EXAMPLE 1

Cloning SPP-Encoding Sequences from Solanaceae

To deduce SPP-encoding DNA sequences, the 6-frame translation of the EST database (GenBank) was screened with the aid of the BLAST algorithm (Altschul et al. 1990, J. Mol. Biol. 215, pp. 403-410) and the protein sequence of the *Arabidopsis thaliana* SPP1 (Acc. No. AF283565). In doing so, several significant hits were identified, inter alia from tomato (*Lycopersicon esculentum*) and potato (*Solanum tuberosum*). The hits from the first round were employed for further database searches using the above mode until the entire coding region of a potential SPP was covered by overlapping tomato or potato ESTs. The primers

```
                                        (SEQ ID NO:8)
FB 223   5'-ATG GAT CAG CTA ACC AGTCGCC GCA C-3'

(SEQ ID NO:9)
FB 224   5'-CTA AAA GAA CCA GGA CGC GGA GTC ACT-3'
``` which flank the entire coding region were deduced from the resulting sequence information. These primers were employed in a standard PCR reaction, for example by the method of T. Maniatis, E. F. Fritsch and J. Sambrook, "Molecular Cloning: A Laboratory Manual", Cold Spring Harbor Laboratory, Cold Spring Harbor, N.Y. (1989), in order to isolate SPP-encoding sequences from cDNA libraries from tobacco and potato (generated by standard methods using the lambda-ZAP kit from Stratagene). Two different clones were isolated from the tobacco cDNA library (SEQ ID NO:1, SEQ ID NO:3) and one clone was isolated from the potato cDNA library (SEQ ID NO:5). The potato clone was completed by means of RACE PCR (prepared by standard methods using the Clontech "Smart™ RACE cDNA Amplification Kit").

EXAMPLE 2

Generation of the Plasmid pBinNtSPP-RNAi

The in vivo function of the sucrose 6-phosphatase activity (SPP activity) was analyzed by the targeted suppression of SPP gene expression in transgenic plants. To generate a construct based on SEQ ID NO:1 which is suitable for this purpose, the first intron of GA20 oxidase from *Solanum* tuberosum (StGA20oxIN, SEQ ID NO:7) was first amplified using the primers

```
GAIN-1  5'-CCT GCA GGC TCG AGA CTA     (SEQ ID NO:10)
        GTA GAT CTG GTA CCG ACC
        GTA CTA CTC TA-3'
and GAIN-2  (5'-CCT GCA GGG TCG ACT CTA    (SEQ ID NO:11)
        GAG GAT CCC CTA TAT AAT TTA
        AGT GGA AAA-3')
``` via PCR under standard conditions (for example as described by T. Maniatis, E. F. Fritsch and J. Sambrook, "Molecular Cloning: A Laboratory Manual", Cold Spring Harbor Laboratory, Cold Spring Harbor, N.Y. (1989)), so that the cleavage sites PstI/SbfI-XhoI-SpeI-BglII was attached at the 5' end and the cleavage sites BamHI-XbaI-SalI-PstI/SbfI were attached at the 3' end. The resulting PCR fragment was subcloned into a pCR-Blunt vector (pCR-Blunt-GA20) and, following digestion with StuI, the Blunt end of pCR-Blunt-GA20 was ligated into a pUC18 vector which had previously been opened by digestion with EcoRI/HindIII and filled up with PFU polymerase following the manufacturer's instructions. The resulting vector pUC-RNAi was employed as template in a PCR under standard conditions (for example as described by T. Maniatis, E. F. Fritsch and J. Sambrook, "Molecular Cloning: A Laboratory Manual", Cold Spring Harbor Laboratory, Cold Spring Harbor, N.Y. (1989)) using the primers

```
FB228   5'-GGA TCC ATG GAT CAG CTA    (SEQ ID NO:12)
        ACC AGT GCC -3'
and

FB229   5-GTC GAC TAC CAT TAC ACC ATA (SEQ ID NO:13)
        ACA CAT C -3'
``` in which process a 660 bp fragment of SEQ ID NO:1 (bp 1-660) which was provided with terminal BamHI/SalI restriction cleavage sites was amplified. The amplified fragment (NtSSP2) was first cloned in antisense orientation (a) into pUC-RNAi which had been opened with BglII/XhoI (yielding vector pUC-RNAi-aNtSSP2). The same fragment was subsequently cloned in sense orientation into the vector pUC-RNAi-aNtSSP2 using BamHI/SalI (yielding the vector pUC-RNAi-aNtSSP2-StGA20oxIN-sNtSSP2). The resulting cassette was ligated into an-SBfI-cut BinAR via PstI from the vector pUC-RNAi-aNtSSP2-StGA20oxIN-sNtSSP2, yielding the plasmid pBinNtSPP-RNAi.

EXAMPLE 3

Transformation and Analysis of Tobacco Plants

The construct pBinNtSPP-RNAi was transformed into the *Agrobacterium tumefaciens* strain C58Cl:pGV2260 by the method of Deblaere et al. (Nucl. Acids. Res. 13(1984), 4777-4788) and incubated with streptomycin/spectinomycin selection. Material used for the transformation of tobacco plants of the variety *Nicotiana tabacum* cv. Samsun NN with the construct pBinNtSPP-RNAi was an overnight culture of a positively transformed agrobacterial colony diluted with YEB medium (5 g/l beef extract, 1 g/l yeast extract, 5 g/l peptone, 5 g/l sucrose, pH 7.2) to $OD_{600}$=0.8-1.6. Leaf disks of sterile plants (approx. 1 cm² each) were incubated for 5-10 minutes in a Petri dish with the agrobacterial overnight culture which had been diluted to $OD_{600}$32 0.8-1.6, followed by incubation for 2 days in the dark at 25° C. on Murashige-Skoog medium (Murashige-Skoog, Physiol. Plant. 15(1962), 473) supplemented with 2% sucrose (2MS medium) and 0.8% Bacto agar). Culturing was continued with 16-hour-light/8-hour-darkness for/over a period of several weeks. The leaf disks/calli were transferred weekly to fresh MS medium supplemented with 500 mg/l Claforan (cefotaxime sodium), 50 mg/l kanamycin, 1 mg/l benzylaminopurin (BAP), 0.2 mg/l naphthylacetic acid and 1.6 g/l glucose. Regenerated shoots were transferred to MS medium supplemented with 2% sucrose, 250 mg/l Claforan and 0.8% Bacto agar and subsequently selected on 2MS medium with kanamycin and Claforan. The resulting transgenic plants were transplanted into soil and observed for 2-20 weeks in the greenhouse for the manifestation of phenotypes. It emerged that the transgenic plants showed pronounced growth retardation symptoms, chlorotic leaves and, in individual cases, necroses. Semiquantitative PCR was used to demonstrate that SPP expression in plants with these phenotypes was suppressed by different degrees, thus demonstrating the relationship between plant growth and SPP expression.

20 µg of total RNA from selected lines (lines 10, 16, 18, 31) and from a nontransgenic control (WT) were first digested for 45 minutes at 37° C. with DNase (Böhringer Mannheim) and subsequently incubated for 10 minutes at 65° C. After treatment with phenol/choroform/isoamyl alcohol (25:24:1), the RNA was precipitated with sodium acetate, washed with 70% ethanol and dissolved in 100 µl of DEPC-treated $H_{20}$. The cDNA first-strand synthesis was carried out in a reaction with 12.5 µl of DNase-treated RNA, 5 µl of 5× reaction buffer, 2 µl of dNTPs (2.5 mM), 1 µl of oligo-dT primer (50 mM, dT[30]V[G/C/A]) and 2.5 µl of DEPC-treated $H_2O$ after incubation for 5 minutes at 65° C., then for 5 minutes at 37° C. and, finally, after addition of 1 µl of reverse transcriptase (Moloney Murine Leukemia Virus Reverse Transcriptase, Rnase H Minus, M-MLV [H–], Promega) and 1 µl of RNAse inhibitor at 37° C. (60 min). After heat inactivation for 5 minutes at 95° C., the cDNA was employed as template for the subsequent PCR. NtSPP cDNA was amplified with the 5' primer CS36 (5'-GTT AGT GTT CTC AAC TGG GAG ATC ACC-3') (SEQ ID NO:14) and the 3' primer CS37 (5'-CCC ATT TCT TGA AAC TCA CTA ACC ATG A-3') (SEQ ID NO:15), and the internal standard actin was amplified with the primer pair $D_2O_2$ (5'-ATG GCA GAC GGT GAG GAT ATT CA-3') (SEQ ID NO:16) and D203 (5'-GCC TTT GCA ATC CAC ATC TGT TG-3') (SEQ ID NO:17) (like AC1 and AC2, Romeis et al. 2001, EMBO J 20: 5556). The PCR reactions (total volume 100 µl) were composed as follows: 70 µl $H_2O$, 5 µl CS36 5'Primer (5 µM), 5 µl 3' primer CS37 (5 µM), 8 µl dNTPs (2.5 mM), 10 µl 10× reaction buffer, 1 µl cDNA and 5 U rTaq DNA polymerase (Takara Shouzo, Japan). Before the beginning of the amplification cycles, the reactions were heated for 5 minutes at 95° C. The polymerization steps were carried out in an automated T3 thermocycler (Biometra) using the following program: denaturing 95° C. (1 min), primer annealing at 55° C. (45 seconds), polymerase reaction at 72° C. (2 min). After 25, 30 and 45 cycles, in each case 10 µl of the PCR reaction were applied to a gel. When the NtSPP-specific primers are used, the result in the nonsaturated PCR range (35 cycles) reveals only the amplification of products in the wild-type controls and not in 3 of the 4 transgenic lines, which suggests highly effective silencing. The PCR with the actin-specific primers, in contrast, reveals uniform DNA bands in the unsaturated range of 35 cycles, which confirms the use of comparable amounts of template employed.

These results of the mRNA level were confirmed by Western blot experiments. Within these experiments, in each case 50 μg of total protein extracts from leaves of the transgenic plants and from wild-type plants were separated on 10% SDS polyacrylamide gels. NtSSP was detected after transfer to nitrocellulose membranes and incubation with a rabbit anti-SSP antibody by means of the ECL method (Amersham Pharmacia, Biotech, according to manufacturer's instructions). Here, NtSSP was not detectable in the transgenic plants, in contrast to wild-type plants. Furthermore, the NtSSP activity was determined in total protein extracts from leaves of the transgenic plants and wild-type plants as described in Example 6. In transgenic plants, the residual activity was 6-10% of the wild-type activity.

EXAMPLE 4

Preparation of Constructs for the Expression of SPP in E. coli

To express the N. tabaccum sucrose-6-phosphatase (N. tabacum SPP2) in E. coli, SEQ ID NO:1 was amplified by PCR using the primers

```
FB228  5'-GGA TCC ATG GAT CAG CTA      (SEQ ID NO:18)
       ACC AGT GCC -3'

SPPr   5'-GTC GAC CTA AAA GAA CCA      (SEQ ID NO:19)
       GGA CGC GGA GTC ACT-3'
``` and the Nicotiana tabacum cDNA library as template, the primers introducing a BamHI and SalI recognition site, respectively, into the sequence. After ligation into the vector pCR-Blunt, the resulting fragment was excized using BamHI and SalI and ligated into the vector pQE-9, which had likewise been cleaved with BamHI and SalI (construct pQE-NtSPP2).

EXAMPLE 5

Expression of NtSPP2 in E. coli

The recombinant protein was expressed in accordance with the manufacturer's instructions (Qiagen, Hilden, Germany) in a 50-ml culture scale. After the cells had been harvested by centrifugation, the precipitate was resuspended in 1 ml of 30 mM HEPES KOH (N-2-hydroxyethylpiperazin-N'-2-ethanesulfonic acid) (pH 7.5), the soluble protein fraction was liberated by sonication and the supernatant obtained after centrifugation was employed for determining the enzyme activity.

EXAMPLE 6

Determination of the sucrose-6-phosphatase (SPP) Activity

SPP activity in protein extracts was detected by measuring the inorganic phosphate liberated by the enzyme from sucrose-6-phosphate, following the method of Lunn et al. (2000, Procl. Natl. Acad. Sci. USA 97: 12914). To this end, enzyme extracts are incubated in a reaction comprising 1.25 mM sucrose-6-phosphate and 8 mM $MgCl_2$ in 25 mM HEPES-KOH, pH 7.0, in a total volume of 300 μl at 30° C. The reaction is quenched by addition of 30 μl of 2M trichloroacetic acid. The orthophosphate liberated from S-6-P during the reaction is determined quantitatively using the ascorbate/ammonium molybdate reagent (of Ames 1966, Methods Enzymol. 8, 115). The detection was carried out in miniaturized form, such as, for example, in 96-well and 384-well microtiter plates.

We claim:

1. A method of identifying herbicidally active compounds, comprising:
   i. bringing an isolated polypeptide with the biological activity of a sucrose-6-phosphate phosphatase encoded by a nucleic acid molecule, wherein the nucleic acid molecule comprises:
      a) a nucleic acid molecule having the nucleic acid sequence of SEQ ID NO: 1;
      b) a nucleic acid molecule having a nucleic acid sequence differing from the nucleic acid sequence of (a) above in codon sequence due to the degeneracy of the genetic code;
      c) a nucleic acid molecule having a nucleic acid sequence having at least 95% identity with SEQ ID NO:1, wherein the nucleic acid sequence encodes a polypeptide having sucrose-6-phosphate phosphatase activity;
      d) a nucleic acid molecule which encodes a polypeptide having the amino acid sequence of SEQ ID NO: 2; or
      e) a nucleic acid molecule which encodes a polypeptide having an amino acid sequence having at least 95% identity with SEQ ID NO: 2, wherein the nucleic acid sequence encodes a polypeptide having sucrose-6-phosphate phosphatase activity;

into contact with one or more test compounds under conditions which permit the test compound(s) to bind to the nucleic acid molecule or to sucrose-6-phosphate phosphatase; and ii. detecting whether the test compound binds to the sucrose-6-phosphate phosphatase of i); or iii. detecting whether the test compound reduces or blocks the transcription, translation or expression of the sucrose-6-phosphate phosphatase of i).

2. A method as claimed in claim 1, which comprises
i. either expressing, in a transgenic organism, sucrose-6-phosphate phosphatase encoded by a nucleic acid molecule, wherein the nucleic acid molecule comprises:
   a) a nucleic acid molecule having the nucleic acid sequence of SEQ ID NO: 1;
   b) a nucleic acid molecule having a nucleic acid sequence differing from the nucleic acid sequence of (a) above in codon sequence due to the degeneracy of the genetic code;
   c) a nucleic acid molecule having a nucleic acid sequence having at least 95% identity with SEQ ID NO:1, wherein the nucleic acid sequence encodes a polypeptide having sucrose-6-phosphate phosphatase activity;
   d) a nucleic acid molecule which encodes a polypeptide having the amino acid sequence of SEQ ID NO: 2; or
   e) a nucleic acid molecule which encodes a polypeptide having an amino acid sequence having at least 95% identity with SEQ ID NO: 2, wherein the nucleic acid sequence encodes a polypeptide having sucrose-6-phosphate phosphatase activity; or
culturing an organism which naturally contains sucrose-6-phosphate phosphatase;

ii. bringing the sucrose-6-phosphate phosphatase of step i) in the cell digest of the transgenic or nontransgenic organism, in partially or homogeneously purified form, into contact with a test compound; and iii. selecting a test compound which reduces or blocks the activity of the sucrose-6-phosphate phosphatase of step a), where the activity of the sucrose-6-phosphate phosphatase incubated with the test compound is compared with the activity of a sucrose-6-phosphate phosphatase which has not been incubated with a test compound.

3. A method as claimed in claim 2, wherein, in step iii), the activity is determined by employing sucrose-6-phosphate as substrate and the orthophosphate which is formed in the reaction is determined quantitatively by means of ammonium molybdate.

4. A method as claimed in claim 1, further comprising
i. generating a nonhuman transgenic organism selected from the group consisting of bacteria, yeasts, fungi, animal cells and plant cells, comprising a nucleic acid molecule encoding a polypeptide with the biological activity of a sucrose-6-phosphate phosphatase, wherein the nucleic acid molecule comprises:
   a) a nucleic acid molecule having the nucleic acid sequence of SEQ ID NO: 1;
   b) a nucleic acid molecule having a nucleic acid sequence differing from the nucleic acid sequence of (a) above in codon sequence due to the degeneracy of the genetic code;
   c) a nucleic acid molecule having a nucleic acid sequence having at least 95% identity with SEQ ID NO:1, wherein the nucleic acid sequence encodes a polypeptide having sucrose-6-phosphate phosphatase activity;
   d) a nucleic acid molecule which encodes a polypeptide having the amino acid sequence of SEQ ID NO: 2; or
   e) a nucleic acid molecule which encodes a polypeptide having an amino acid sequence having at least 95% identity with SEQ ID NO: 2, wherein the nucleic acid sequence encodes a polypeptide having sucrose-6-phosphate phosphatase activity;

ii. applying a test compound to the transgenic organism of i) and to a nontransgenic organism of the same genotype; and iii. determining the growth or the viability of the transgenic and the nontransgenic organisms after application of the test compound; and iv. thereby selecting test compounds which bring about reduced growth or reduced viability of the nontransgenic organism in comparison with the growth of the transgenic organism.

5. A method as claimed in claim 4, which is carried out in a plant organism, a cyanobacterium or a proteobacterium.

6. A method as claimed in claim 1, 2 or 3, wherein the compounds are identified in a high-throughput screening.

7. The method of claim 4, wherein the nucleic acid sequence encoding the polypeptide sequence is in an expression cassette comprising genetic control sequences in operable linkage with the nucleic acid sequence.

8. The method of claim 7, wherein the expression cassette is contained in a vector.

* * * * *

SEQUENCE LISTING

<160> NUMBER OF SEQ ID NOS: 19

<210> SEQ ID NO 1
<211> LENGTH: 1278
<212> TYPE: DNA
<213> ORGANISM: Nicotiana tabacum
<220> FEATURE:
<221> NAME/KEY: CDS
<222> LOCATION: (1)..(1275)
<223> OTHER INFORMATION:

<400> SEQUENCE: 1

```
atg gat cag cta acc agt gcc gca cgt ctc atg ata gtc tca gat cta      48
Met Asp Gln Leu Thr Ser Ala Ala Arg Leu Met Ile Val Ser Asp Leu
1               5                   10                  15 gac cat aca atg gta gat cat cat gat gcc gag aac ctt tct ctg ctt      96
Asp His Thr Met Val Asp His His Asp Ala Glu Asn Leu Ser Leu Leu
                20                  25                  30 aga ttt aat gct tta tgg gag gcg aat tat cgt gat aac tct ttg tta    144
Arg Phe Asn Ala Leu Trp Glu Ala Asn Tyr Arg Asp Asn Ser Leu Leu
            35                  40                  45 gtg ttc tca act ggg aga tca cct aca ctt tac aag gag ttg agg aaa    192
Val Phe Ser Thr Gly Arg Ser Pro Thr Leu Tyr Lys Glu Leu Arg Lys
        50                  55                  60
```

-continued

| | | |
|---|---|---|
| gaa aag ccc atg cta acc cca gat att act att atg tcg gtg gga act<br>Glu Lys Pro Met Leu Thr Pro Asp Ile Thr Ile Met Ser Val Gly Thr<br>65                    70                    75                    80 | | 240 |
| gaa ata aca tat ggt aac tct gtg gtg cct gat gat ggt tgg gaa gct<br>Glu Ile Thr Tyr Gly Asn Ser Val Val Pro Asp Asp Gly Trp Glu Ala<br>                    85                    90                    95 | | 288 |
| ttt cta aat aac aag tgg gac aga aag ata gta aca gag gag act agc<br>Phe Leu Asn Asn Lys Trp Asp Arg Lys Ile Val Thr Glu Glu Thr Ser<br>           100                    105                    110 | | 336 |
| aag ttt cct gaa ctc act cta cag tca gaa acg gag cag cga cca cac<br>Lys Phe Pro Glu Leu Thr Leu Gln Ser Glu Thr Glu Gln Arg Pro His<br>           115                    120                    125 | | 384 |
| aag gtc agt ttc tat gtt cag aaa gac aaa gca caa gat ata atg aaa<br>Lys Val Ser Phe Tyr Val Gln Lys Asp Lys Ala Gln Asp Ile Met Lys<br>130                    135                    140 | | 432 |
| act ctt tcc aag cgc ttc gaa gaa cgt ggg ctg gat gtc aaa ata att<br>Thr Leu Ser Lys Arg Phe Glu Glu Arg Gly Leu Asp Val Lys Ile Ile<br>145                    150                    155                    160 | | 480 |
| tac agt gga ggc atg gat cta gat ata tta cca caa ggt gct ggc aaa<br>Tyr Ser Gly Gly Met Asp Leu Asp Ile Leu Pro Gln Gly Ala Gly Lys<br>                    165                    170                    175 | | 528 |
| gga caa gca ctt gca tat ttg ctt aag aaa ttg aag agt gag gga aaa<br>Gly Gln Ala Leu Ala Tyr Leu Leu Lys Lys Leu Lys Ser Glu Gly Lys<br>           180                    185                    190 | | 576 |
| tta cca aac aac acc ctt gcc tgt ggt gac tct ggg aat gat gct gag<br>Leu Pro Asn Asn Thr Leu Ala Cys Gly Asp Ser Gly Asn Asp Ala Glu<br>           195                    200                    205 | | 624 |
| cta ttc agt atc cca gat gtg tat ggt gta atg gta gct aat gca cag<br>Leu Phe Ser Ile Pro Asp Val Tyr Gly Val Met Val Ala Asn Ala Gln<br>210                    215                    220 | | 672 |
| gag gaa tta ttg caa tgg cat gct gca aat gcg aag aat aat cct aaa<br>Glu Glu Leu Leu Gln Trp His Ala Ala Asn Ala Lys Asn Asn Pro Lys<br>225                    230                    235                    240 | | 720 |
| gta att cat gca aca gag agg tgt gct gcc ggt atc ata caa gct att<br>Val Ile His Ala Thr Glu Arg Cys Ala Ala Gly Ile Ile Gln Ala Ile<br>                    245                    250                    255 | | 768 |
| ggt cat tcc aac cta ggt cca agt acc tcc cct aga gat gtt atg gat<br>Gly His Ser Asn Leu Gly Pro Ser Thr Ser Pro Arg Asp Val Met Asp<br>           260                    265                    270 | | 816 |
| ttg tca gac tgc aag atg gag aac ttt gtt ccc gcc tat gaa gtt gtc<br>Leu Ser Asp Cys Lys Met Glu Asn Phe Val Pro Ala Tyr Glu Val Val<br>           275                    280                    285 | | 864 |
| aaa ttt tac cta ttt ttt gag aaa tgg agg cgt gga gaa att gag cat<br>Lys Phe Tyr Leu Phe Phe Glu Lys Trp Arg Arg Gly Glu Ile Glu His<br>290                    295                    300 | | 912 |
| tct gag cat tac ctg tca aac ctt aaa gca gtg tgt aga cca tct ggt<br>Ser Glu His Tyr Leu Ser Asn Leu Lys Ala Val Cys Arg Pro Ser Gly<br>305                    310                    315                    320 | | 960 |
| act ttt gtc cac cca tct ggt gtt gag aaa tcc ctc cag gaa tgt gta<br>Thr Phe Val His Pro Ser Gly Val Glu Lys Ser Leu Gln Glu Cys Val<br>           325                    330                    335 | | 1008 |
| act tta ttc ggg aca tgt cat ggt gac aaa cag ggg aaa caa ttt cgt<br>Thr Leu Phe Gly Thr Cys His Gly Asp Lys Gln Gly Lys Gln Phe Arg<br>           340                    345                    350 | | 1056 |
| att tgg gtc gat caa gtt tta cct gta cag gtt ggt tcg gac tca tgg<br>Ile Trp Val Asp Gln Val Leu Pro Val Gln Val Gly Ser Asp Ser Trp<br>           355                    360                    365 | | 1104 |
| tta gtg agt ttc aag aaa tgg gag ctc tct ggt gaa gac agg cga tgt<br>Leu Val Ser Phe Lys Lys Trp Glu Leu Ser Gly Glu Asp Arg Arg Cys | | 1152 |

```
             370                 375                 380
tgc ata act aca gtc cta tta agt tca aag aat aag act gtc gca gat   1200
Cys Ile Thr Thr Val Leu Leu Ser Ser Lys Asn Lys Thr Val Ala Asp
385                 390                 395                 400 gga ctc act tgg acc cac gta cat cag aca tgg ctg aat gga gct gca   1248
Gly Leu Thr Trp Thr His Val His Gln Thr Trp Leu Asn Gly Ala Ala
                    405                 410                 415 gca agt gac tcc gcg tcc tgg ttc ttt tag                           1278
Ala Ser Asp Ser Ala Ser Trp Phe Phe
                420                 425

<210> SEQ ID NO 2
<211> LENGTH: 425
<212> TYPE: PRT
<213> ORGANISM: Nicotiana tabacum

<400> SEQUENCE: 2

Met Asp Gln Leu Thr Ser Ala Ala Arg Leu Met Ile Val Ser Asp Leu
1               5                   10                  15

Asp His Thr Met Val Asp His His Asp Ala Glu Asn Leu Ser Leu Leu
            20                  25                  30

Arg Phe Asn Ala Leu Trp Glu Ala Asn Tyr Arg Asp Asn Ser Leu Leu
        35                  40                  45

Val Phe Ser Thr Gly Arg Ser Pro Thr Leu Tyr Lys Glu Leu Arg Lys
50                  55                  60

Glu Lys Pro Met Leu Thr Pro Asp Ile Thr Ile Met Ser Val Gly Thr
65                  70                  75                  80

Glu Ile Thr Tyr Gly Asn Ser Val Val Pro Asp Asp Gly Trp Glu Ala
            85                  90                  95

Phe Leu Asn Asn Lys Trp Asp Arg Lys Ile Val Thr Glu Glu Thr Ser
        100                 105                 110

Lys Phe Pro Glu Leu Thr Leu Gln Ser Glu Thr Glu Gln Arg Pro His
    115                 120                 125

Lys Val Ser Phe Tyr Val Gln Lys Asp Lys Ala Gln Asp Ile Met Lys
130                 135                 140

Thr Leu Ser Lys Arg Phe Glu Glu Arg Gly Leu Asp Val Lys Ile Ile
145                 150                 155                 160

Tyr Ser Gly Gly Met Asp Leu Asp Ile Leu Pro Gln Gly Ala Gly Lys
                165                 170                 175

Gly Gln Ala Leu Ala Tyr Leu Leu Lys Lys Leu Lys Ser Glu Gly Lys
            180                 185                 190

Leu Pro Asn Asn Thr Leu Ala Cys Gly Asp Ser Gly Asn Asp Ala Glu
        195                 200                 205

Leu Phe Ser Ile Pro Asp Val Tyr Gly Val Met Val Ala Asn Ala Gln
    210                 215                 220

Glu Glu Leu Leu Gln Trp His Ala Ala Asn Ala Lys Asn Asn Pro Lys
225                 230                 235                 240

Val Ile His Ala Thr Glu Arg Cys Ala Ala Gly Ile Ile Gln Ala Ile
                245                 250                 255

Gly His Ser Asn Leu Gly Pro Ser Thr Ser Pro Arg Asp Val Met Asp
            260                 265                 270

Leu Ser Asp Cys Lys Met Glu Asn Phe Val Pro Ala Tyr Glu Val Val
        275                 280                 285

Lys Phe Tyr Leu Phe Phe Glu Lys Trp Arg Arg Gly Glu Ile Glu His
    290                 295                 300
```

```
Ser Glu His Tyr Leu Ser Asn Leu Lys Ala Val Cys Arg Pro Ser Gly
305                 310                 315                 320

Thr Phe Val His Pro Ser Gly Val Glu Lys Ser Leu Gln Glu Cys Val
            325                 330                 335

Thr Leu Phe Gly Thr Cys His Gly Asp Lys Gln Gly Lys Gln Phe Arg
                340                 345                 350

Ile Trp Val Asp Gln Val Leu Pro Val Gln Val Gly Ser Asp Ser Trp
            355                 360                 365

Leu Val Ser Phe Lys Lys Trp Glu Leu Ser Gly Glu Asp Arg Arg Cys
            370                 375                 380

Cys Ile Thr Thr Val Leu Ser Ser Lys Asn Lys Thr Val Ala Asp
385                 390                 395                 400

Gly Leu Thr Trp Thr His Val His Gln Thr Trp Leu Asn Gly Ala Ala
                405                 410                 415

Ala Ser Asp Ser Ala Ser Trp Phe Phe
            420                 425

<210> SEQ ID NO 3
<211> LENGTH: 1278
<212> TYPE: DNA
<213> ORGANISM: Nicotiana tabacum
<220> FEATURE:
<221> NAME/KEY: CDS
<222> LOCATION: (1)..(1275)
<223> OTHER INFORMATION:

<400> SEQUENCE: 3 atg gat cag cta acc agt gcc gca cgt ctc atg ata gtc tca gat ctt    48
Met Asp Gln Leu Thr Ser Ala Ala Arg Leu Met Ile Val Ser Asp Leu
1               5                   10                  15 gac cat acc atg gtt gat cat cat gat cct gag aac ctt tct ctg ctt    96
Asp His Thr Met Val Asp His His Asp Pro Glu Asn Leu Ser Leu Leu
                20                  25                  30 agg ttt aat gct tta tgg gag gcc aat tat cgt gaa aac tcc ttg tta   144
Arg Phe Asn Ala Leu Trp Glu Ala Asn Tyr Arg Glu Asn Ser Leu Leu
            35                  40                  45 gtg ttc tca act ggg aga tca cct acc ctt tac aag gag ttg aga aaa   192
Val Phe Ser Thr Gly Arg Ser Pro Thr Leu Tyr Lys Glu Leu Arg Lys
        50                  55                  60 gag aag ccc atg cta acc cca gat att acc att atg tct gtg ggg act   240
Glu Lys Pro Met Leu Thr Pro Asp Ile Thr Ile Met Ser Val Gly Thr
65                  70                  75                  80 gaa ata act tat ggt aac tct atg gag cca gat gat ggt tgg gaa gca   288
Glu Ile Thr Tyr Gly Asn Ser Met Glu Pro Asp Asp Gly Trp Glu Ala
                85                  90                  95 ttt tta aat gat aag tgg gat cgg aaa ata gtg aca gag gag aca agc   336
Phe Leu Asn Asp Lys Trp Asp Arg Lys Ile Val Thr Glu Glu Thr Ser
            100                 105                 110 aaa ttt cct gaa ctc acc ctt cag tca gaa aca gag cag cga cca cac   384
Lys Phe Pro Glu Leu Thr Leu Gln Ser Glu Thr Glu Gln Arg Pro His
        115                 120                 125 aag gtc agt ttc tat gtt cag aaa gac aag gct caa gat ata acg gga   432
Lys Val Ser Phe Tyr Val Gln Lys Asp Lys Ala Gln Asp Ile Thr Gly
    130                 135                 140 act ctt tcc aag cgc ttg gaa gaa cgt ggg ttg gat gtc aaa ata att   480
Thr Leu Ser Lys Arg Leu Glu Glu Arg Gly Leu Asp Val Lys Ile Ile
145                 150                 155                 160 tat agc gga ggg atg gat ttg gac att ttg cca caa ggt gct ggc aaa   528
Tyr Ser Gly Gly Met Asp Leu Asp Ile Leu Pro Gln Gly Ala Gly Lys
                165                 170                 175
```

```
gga cga gca ctt gca tat ttg ctt aag aaa tta aag agt gag ggc aag      576
Gly Arg Ala Leu Ala Tyr Leu Leu Lys Lys Leu Lys Ser Glu Gly Lys
        180                 185                 190 tta cca aac aac acg ctt gcc tgt ggt gac tct gga aat gat gct gag      624
Leu Pro Asn Asn Thr Leu Ala Cys Gly Asp Ser Gly Asn Asp Ala Glu
    195                 200                 205 ctt ttc agt atc cca gat gtt tat ggt gtg atg gta gcg aat gca cag      672
Leu Phe Ser Ile Pro Asp Val Tyr Gly Val Met Val Ala Asn Ala Gln
210                 215                 220 gag gag tta tta caa tgg cgt gct gca aat gca aaa gat agt cca aaa      720
Glu Glu Leu Leu Gln Trp Arg Ala Ala Asn Ala Lys Asp Ser Pro Lys
225                 230                 235                 240 gta att cat gca aca gag aga tgt gcc gcg ggt ata ata caa gca att      768
Val Ile His Ala Thr Glu Arg Cys Ala Ala Gly Ile Ile Gln Ala Ile
            245                 250                 255 ggg cat ttc aac ctg gga cca aat acc tct cct aga gat gtt aca gat      816
Gly His Phe Asn Leu Gly Pro Asn Thr Ser Pro Arg Asp Val Thr Asp
        260                 265                 270 atg tca gac tgc aag atg gag aat ttt gtt cct gct tat gaa gtc gtc      864
Met Ser Asp Cys Lys Met Glu Asn Phe Val Pro Ala Tyr Glu Val Val
    275                 280                 285 aaa ttt tac ttg ttt ttc gag aaa tgg agg cgt gga gaa att gag aat      912
Lys Phe Tyr Leu Phe Phe Glu Lys Trp Arg Arg Gly Glu Ile Glu Asn
290                 295                 300 tct gac ctt cac ttg tca aac ctg aaa gca gtt tgt aga cca tcc ggt      960
Ser Asp Leu His Leu Ser Asn Leu Lys Ala Val Cys Arg Pro Ser Gly
305                 310                 315                 320 act ttt gtg cac cca tct gga gtt gag aaa tat ctt gag gac tgc ata     1008
Thr Phe Val His Pro Ser Gly Val Glu Lys Tyr Leu Glu Asp Cys Ile
            325                 330                 335 aat aca ttg aga act tgt cac ggt gac aaa cag ggt aaa caa ttt cgt     1056
Asn Thr Leu Arg Thr Cys His Gly Asp Lys Gln Gly Lys Gln Phe Arg
        340                 345                 350 att tgg gtt gat cta gtg tta cct aca cag gtt ggt tca gat tca tgg     1104
Ile Trp Val Asp Leu Val Leu Pro Thr Gln Val Gly Ser Asp Ser Trp
    355                 360                 365 tta gtg agt ttc aag aaa tgg gag ctt tgt ggc gaa gag cga caa tgt     1152
Leu Val Ser Phe Lys Lys Trp Glu Leu Cys Gly Glu Glu Arg Gln Cys
370                 375                 380 tgc ata act act gtc ttg tta agt tca aag aat gtg acg gtc gcg gat     1200
Cys Ile Thr Thr Val Leu Leu Ser Ser Lys Asn Val Thr Val Ala Asp
385                 390                 395                 400 ggg ctc act tgg aca cat gtg cat cag act tgg ctg cag gga gca gca     1248
Gly Leu Thr Trp Thr His Val His Gln Thr Trp Leu Gln Gly Ala Ala
            405                 410                 415 gca agt gac tcc gcg tcc tgg ttc ttt taa                             1278
Ala Ser Asp Ser Ala Ser Trp Phe Phe
        420                 425

<210> SEQ ID NO 4
<211> LENGTH: 425
<212> TYPE: PRT
<213> ORGANISM: Nicotiana tabacum

<400> SEQUENCE: 4

Met Asp Gln Leu Thr Ser Ala Ala Arg Leu Met Ile Val Ser Asp Leu
1               5                   10                  15

Asp His Thr Met Val Asp His His Asp Pro Glu Asn Leu Ser Leu Leu
            20                  25                  30
```

```
Arg Phe Asn Ala Leu Trp Glu Ala Asn Tyr Arg Glu Asn Ser Leu Leu
         35                  40                  45

Val Phe Ser Thr Gly Arg Ser Pro Thr Leu Tyr Lys Glu Leu Arg Lys
 50                  55                  60

Glu Lys Pro Met Leu Thr Pro Asp Ile Thr Ile Met Ser Val Gly Thr
 65                  70                  75                  80

Glu Ile Thr Tyr Gly Asn Ser Met Glu Pro Asp Asp Gly Trp Glu Ala
                 85                  90                  95

Phe Leu Asn Asp Lys Trp Asp Arg Lys Ile Val Thr Glu Glu Thr Ser
                100                 105                 110

Lys Phe Pro Glu Leu Thr Leu Gln Ser Glu Thr Glu Gln Arg Pro His
            115                 120                 125

Lys Val Ser Phe Tyr Val Gln Lys Asp Lys Ala Gln Asp Ile Thr Gly
        130                 135                 140

Thr Leu Ser Lys Arg Leu Glu Glu Arg Gly Leu Asp Val Lys Ile Ile
145                 150                 155                 160

Tyr Ser Gly Gly Met Asp Leu Asp Ile Leu Pro Gln Gly Ala Gly Lys
                165                 170                 175

Gly Arg Ala Leu Ala Tyr Leu Leu Lys Lys Leu Lys Ser Glu Gly Lys
            180                 185                 190

Leu Pro Asn Asn Thr Leu Ala Cys Gly Asp Ser Gly Asn Asp Ala Glu
        195                 200                 205

Leu Phe Ser Ile Pro Asp Val Tyr Gly Val Met Val Ala Asn Ala Gln
    210                 215                 220

Glu Glu Leu Leu Gln Trp Arg Ala Ala Asn Ala Lys Asp Ser Pro Lys
225                 230                 235                 240

Val Ile His Ala Thr Glu Arg Cys Ala Ala Gly Ile Ile Gln Ala Ile
                245                 250                 255

Gly His Phe Asn Leu Gly Pro Asn Thr Ser Pro Arg Asp Val Thr Asp
            260                 265                 270

Met Ser Asp Cys Lys Met Glu Asn Phe Val Pro Ala Tyr Glu Val Val
        275                 280                 285

Lys Phe Tyr Leu Phe Phe Glu Lys Trp Arg Arg Gly Glu Ile Glu Asn
    290                 295                 300

Ser Asp Leu His Leu Ser Asn Leu Lys Ala Val Cys Arg Pro Ser Gly
305                 310                 315                 320

Thr Phe Val His Pro Ser Gly Val Glu Lys Tyr Leu Glu Asp Cys Ile
                325                 330                 335

Asn Thr Leu Arg Thr Cys His Gly Asp Lys Gln Gly Lys Gln Phe Arg
            340                 345                 350

Ile Trp Val Asp Leu Val Leu Pro Thr Gln Val Gly Ser Asp Ser Trp
        355                 360                 365

Leu Val Ser Phe Lys Lys Trp Glu Leu Cys Gly Glu Glu Arg Gln Cys
    370                 375                 380

Cys Ile Thr Thr Val Leu Leu Ser Ser Lys Asn Val Thr Val Ala Asp
385                 390                 395                 400

Gly Leu Thr Trp Thr His Val His Gln Thr Trp Leu Gln Gly Ala Ala
                405                 410                 415

Ala Ser Asp Ser Ala Ser Trp Phe Phe
            420                 425

<210> SEQ ID NO 5
<211> LENGTH: 1642
<212> TYPE: DNA
```

<213> ORGANISM: Solanum tuberosum
<220> FEATURE:
<221> NAME/KEY: CDS
<222> LOCATION: (70)..(1344)
<223> OTHER INFORMATION:

<400> SEQUENCE: 5

```
acacaaaaaa gatttcattt ttttgtttcc ccaattccca tttcaggttg aagccaattt      60 acatcaatc atg gat cgg cta acc agt gct gca cgt ctc atg ata gtc tca     111
          Met Asp Arg Leu Thr Ser Ala Ala Arg Leu Met Ile Val Ser
          1               5                   10 gat ctt gac cat aca atg gta gat cat cac gat tcc gag aac ctt tct       159
Asp Leu Asp His Thr Met Val Asp His His Asp Ser Glu Asn Leu Ser
15                  20                  25                  30 ctg ctt agg ttc aat gct tta tgg gaa gcc aat tat cgt gat aac tct       207
Leu Leu Arg Phe Asn Ala Leu Trp Glu Ala Asn Tyr Arg Asp Asn Ser
                35                  40                  45 tta tta gtg ttc tct act ggg aga tca cct aca ctt tac aag gaa tta       255
Leu Leu Val Phe Ser Thr Gly Arg Ser Pro Thr Leu Tyr Lys Glu Leu
        50                  55                  60 agg aaa gaa aag ccc atg cta acc cca gat att aca att atg tct gtg       303
Arg Lys Glu Lys Pro Met Leu Thr Pro Asp Ile Thr Ile Met Ser Val
    65                  70                  75 gga act gaa ata aca tat ggt aac gct atg gtg cct gat gat ggt tgg       351
Gly Thr Glu Ile Thr Tyr Gly Asn Ala Met Val Pro Asp Asp Gly Trp
80                  85                  90 gaa aca ttt ctg aat aac aag tgg gat aga aag ata gta aca gag gag       399
Glu Thr Phe Leu Asn Asn Lys Trp Asp Arg Lys Ile Val Thr Glu Glu
95                  100                 105                 110 aca agc aag ttt cct gaa ctc agt ctg cag tca gaa aca gag cag cga       447
Thr Ser Lys Phe Pro Glu Leu Ser Leu Gln Ser Glu Thr Glu Gln Arg
                115                 120                 125 cca cac aag gtc agt ttc tat gtt cag aaa gag aaa gct caa gat ata       495
Pro His Lys Val Ser Phe Tyr Val Gln Lys Glu Lys Ala Gln Asp Ile
        130                 135                 140 atg aaa act ctt tcc aag cgc ttg gaa gaa cgt ggg ctg gat gtc aaa       543
Met Lys Thr Leu Ser Lys Arg Leu Glu Glu Arg Gly Leu Asp Val Lys
    145                 150                 155 ata att tac agt gga ggg atg gat cta gat ata tta cca cag ggt gct       591
Ile Ile Tyr Ser Gly Gly Met Asp Leu Asp Ile Leu Pro Gln Gly Ala
160                 165                 170 ggc aaa gga caa gca ctt gca tat ctg ctt aag aaa ctg aag agc gag       639
Gly Lys Gly Gln Ala Leu Ala Tyr Leu Leu Lys Lys Leu Lys Ser Glu
175                 180                 185                 190 gga aaa tta cca agc aac acc ctt gcc tgc ggc gac tcc ggg aat gac       687
Gly Lys Leu Pro Ser Asn Thr Leu Ala Cys Gly Asp Ser Gly Asn Asp
                195                 200                 205 gct gaa tta ttc agt atc cca gat gtg tat ggt gta atg gta gct aat       735
Ala Glu Leu Phe Ser Ile Pro Asp Val Tyr Gly Val Met Val Ala Asn
        210                 215                 220 gcg cag aag gaa tta ctg cag tgg cat gct gca aat gca aaa aat aat       783
Ala Gln Lys Glu Leu Leu Gln Trp His Ala Ala Asn Ala Lys Asn Asn
    225                 230                 235 ccc aaa gta att cat gca tca gag agg tgt gcc gcc ggt atc ata caa       831
Pro Lys Val Ile His Ala Ser Glu Arg Cys Ala Ala Gly Ile Ile Gln
240                 245                 250 gcc att ggt cat ttc aaa cta ggt cca agt acc tcc cca aga gac gtt       879
Ala Ile Gly His Phe Lys Leu Gly Pro Ser Thr Ser Pro Arg Asp Val
255                 260                 265                 270 acg gat ttg tca gat tgc aag atg gac aac ttt gtt cct gcc tat gaa       927
Thr Asp Leu Ser Asp Cys Lys Met Asp Asn Phe Val Pro Ala Tyr Glu
```

-continued

```
Thr Asp Leu Ser Asp Cys Lys Met Asp Asn Phe Val Pro Ala Tyr Glu
            275                 280                 285 gtt gtc aaa ttt tac ctg ttt ttt gag aaa tgg agg cgt gga gaa att      975
Val Val Lys Phe Tyr Leu Phe Phe Glu Lys Trp Arg Arg Gly Glu Ile
            290                 295                 300 gag cat tct gag cat tat ctg cca aac ctg aaa gca gtg tgt ata cca     1023
Glu His Ser Glu His Tyr Leu Pro Asn Leu Lys Ala Val Cys Ile Pro
            305                 310                 315 tct ggt act ttt gtt cac cca tct ggt gtt gag aaa tcc ctt cag gaa     1071
Ser Gly Thr Phe Val His Pro Ser Gly Val Glu Lys Ser Leu Gln Glu
        320                 325                 330 tgt gta act tca ttc gga aca tgt cat gct gac aag cag ggg aaa caa     1119
Cys Val Thr Ser Phe Gly Thr Cys His Ala Asp Lys Gln Gly Lys Gln
335                 340                 345                 350 tat cgt gtt tgg gtc gat caa gtt tta cct tca cag gtt ggt tca gac     1167
Tyr Arg Val Trp Val Asp Gln Val Leu Pro Ser Gln Val Gly Ser Asp
                355                 360                 365 tca tgg tta gtg agt ttc aag aag tgg gag ctc tct ggt gaa gac atg     1215
Ser Trp Leu Val Ser Phe Lys Lys Trp Glu Leu Ser Gly Glu Asp Met
            370                 375                 380 cga tgc tgc ata acc aca gtc cta tta agt tca aag aat aag act gtt     1263
Arg Cys Cys Ile Thr Thr Val Leu Leu Ser Ser Lys Asn Lys Thr Val
            385                 390                 395 gca gac ggg ctc act tgg act cac gta cat cag aca tgg ctg cac ggt     1311
Ala Asp Gly Leu Thr Trp Thr His Val His Gln Thr Trp Leu His Gly
        400                 405                 410 gat gca gca agt gac tcc gca acc tgg ttc ttt tagattgtca tctcagtgta   1364
Asp Ala Ala Ser Asp Ser Ala Thr Trp Phe Phe
415                 420                 425 ttaactctga aaattccgca ccccttttac cagttcacac ccagaataaa cacaacatac   1424
aaactatagt tgataatcaa tgtattaact ttctccttct ttgataatca atgtattgcc   1484
atctaaacca gtgaagatgg ctttatcttt tgtgtagtat aaagaattat attagtatca   1544
tagttgttct tgtatttgat tcagaattca agatgagatt gttgcaaatt gctgcatatt   1604
taagtttcca aaaaaaaaaa aaaaaaaaaa aaaaaaaa                           1642

<210> SEQ ID NO 6
<211> LENGTH: 425
<212> TYPE: PRT
<213> ORGANISM: Solanum tuberosum

<400> SEQUENCE: 6

Met Asp Arg Leu Thr Ser Ala Ala Arg Leu Met Ile Val Ser Asp Leu
1               5                   10                  15

Asp His Thr Met Val Asp His His Asp Ser Glu Asn Leu Ser Leu Leu
            20                  25                  30

Arg Phe Asn Ala Leu Trp Glu Ala Asn Tyr Arg Asp Asn Ser Leu Leu
        35                  40                  45

Val Phe Ser Thr Gly Arg Ser Pro Thr Leu Tyr Lys Glu Leu Arg Lys
    50                  55                  60

Glu Lys Pro Met Leu Thr Pro Asp Ile Thr Ile Met Ser Val Gly Thr
65                  70                  75                  80

Glu Ile Thr Tyr Gly Asn Ala Met Val Pro Asp Asp Gly Trp Glu Thr
                85                  90                  95

Phe Leu Asn Asn Lys Trp Asp Arg Lys Ile Val Thr Glu Glu Thr Ser
            100                 105                 110

Lys Phe Pro Glu Leu Ser Leu Gln Ser Glu Thr Glu Gln Arg Pro His
```

```
            115                 120                 125
Lys Val Ser Phe Tyr Val Gln Lys Glu Lys Ala Gln Asp Ile Met Lys
            130                 135                 140
Thr Leu Ser Lys Arg Leu Glu Glu Arg Gly Leu Asp Val Lys Ile Ile
145                 150                 155                 160
Tyr Ser Gly Gly Met Asp Leu Asp Ile Leu Pro Gln Gly Ala Gly Lys
                165                 170                 175
Gly Gln Ala Leu Ala Tyr Leu Lys Lys Leu Lys Ser Glu Gly Lys
            180                 185                 190
Leu Pro Ser Asn Thr Leu Ala Cys Gly Asp Ser Gly Asn Asp Ala Glu
            195                 200                 205
Leu Phe Ser Ile Pro Asp Val Tyr Gly Val Met Val Ala Asn Ala Gln
            210                 215                 220
Lys Glu Leu Leu Gln Trp His Ala Ala Asn Ala Lys Asn Asn Pro Lys
225                 230                 235                 240
Val Ile His Ala Ser Glu Arg Cys Ala Ala Gly Ile Ile Gln Ala Ile
                245                 250                 255
Gly His Phe Lys Leu Gly Pro Ser Thr Ser Pro Arg Asp Val Thr Asp
            260                 265                 270
Leu Ser Asp Cys Lys Met Asp Asn Phe Val Pro Ala Tyr Glu Val Val
            275                 280                 285
Lys Phe Tyr Leu Phe Phe Glu Lys Trp Arg Arg Gly Glu Ile Glu His
            290                 295                 300
Ser Glu His Tyr Leu Pro Asn Leu Lys Ala Val Cys Ile Pro Ser Gly
305                 310                 315                 320
Thr Phe Val His Pro Ser Gly Val Glu Lys Ser Leu Gln Glu Cys Val
                325                 330                 335
Thr Ser Phe Gly Thr Cys His Ala Asp Lys Gln Gly Lys Gln Tyr Arg
            340                 345                 350
Val Trp Val Asp Gln Val Leu Pro Ser Gln Val Gly Ser Asp Ser Trp
            355                 360                 365
Leu Val Ser Phe Lys Lys Trp Glu Leu Ser Gly Glu Asp Met Arg Cys
            370                 375                 380
Cys Ile Thr Thr Val Leu Leu Ser Ser Lys Asn Lys Thr Val Ala Asp
385                 390                 395                 400
Gly Leu Thr Trp Thr His Val His Gln Thr Trp Leu His Gly Asp Ala
                405                 410                 415
Ala Ser Asp Ser Ala Thr Trp Phe Phe
            420                 425

<210> SEQ ID NO 7
<211> LENGTH: 199
<212> TYPE: DNA
<213> ORGANISM: Solanum tuberosum

<400> SEQUENCE: 7
gtacggaccg tactactcta ttcgtttcaa tatatttatt tgtttcagct gactgcaaga     60
ttcaaaaatt tctttattat tttaaatttt gtgtcactca aaaccagata aacaatttga    120
tatagagcca ctatatatat acatattctc gattatatat gtaaatgagt tacccttttt    180
ttccacttaa attatatag                                                 199

<210> SEQ ID NO 8
<211> LENGTH: 26
<212> TYPE: DNA
```

<213> ORGANISM: Artificial sequence
<220> FEATURE:
<223> OTHER INFORMATION: Primer

<400> SEQUENCE: 8
atggatcagc taaccagtcg ccgcac                                      26

<210> SEQ ID NO 9
<211> LENGTH: 27
<212> TYPE: DNA
<213> ORGANISM: Artificial sequence
<220> FEATURE:
<223> OTHER INFORMATION: Primer

<400> SEQUENCE: 9
ctaaaagaac caggacgcgg agtcact                                     27

<210> SEQ ID NO 10
<211> LENGTH: 47
<212> TYPE: DNA
<213> ORGANISM: Artificial sequence
<220> FEATURE:
<223> OTHER INFORMATION: Primer

<400> SEQUENCE: 10
cctgcaggct cgagactagt agatctggta cggaccgtac tactcta              47

<210> SEQ ID NO 11
<211> LENGTH: 48
<212> TYPE: DNA
<213> ORGANISM: Artificial sequence
<220> FEATURE:
<223> OTHER INFORMATION: Primer

<400> SEQUENCE: 11
cctgcagggt cgactctaga ggatcccta tataatttaa gtggaaaa              48

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
ggatccatgg atcagctaac cagtgcc                                     27

<210> SEQ ID NO 13
<211> LENGTH: 28
<212> TYPE: DNA
<213> ORGANISM: Artificial sequence
<220> FEATURE:
<223> OTHER INFORMATION: Primer

<400> SEQUENCE: 13
gtcgactacc attacaccat aacacatc                                    28

<210> SEQ ID NO 14
<211> LENGTH: 27
<212> TYPE: DNA
<213> ORGANISM: Artificial sequence
<220> FEATURE:
<223> OTHER INFORMATION: Artificial sequence

<400> SEQUENCE: 14
gttagtgttc tcaactggga gatcacc                                     27

```
<210> SEQ ID NO 15
<211> LENGTH: 28
<212> TYPE: DNA
<213> ORGANISM: Artificial sequence
<220> FEATURE:
<223> OTHER INFORMATION: Primer

<400> SEQUENCE: 15
cccatttctt gaaactcact aaccatga                                          28

<210> SEQ ID NO 16
<211> LENGTH: 23
<212> TYPE: DNA
<213> ORGANISM: Artificial sequence
<220> FEATURE:
<223> OTHER INFORMATION: Primer

<400> SEQUENCE: 16
atggcagacg gtgaggatat tca                                               23

<210> SEQ ID NO 17
<211> LENGTH: 23
<212> TYPE: DNA
<213> ORGANISM: Artificial sequence
<220> FEATURE:
<223> OTHER INFORMATION: Primer

<400> SEQUENCE: 17
gcctttgcaa tccacatctg ttg                                               23

<210> SEQ ID NO 18
<211> LENGTH: 27
<212> TYPE: DNA
<213> ORGANISM: Artificial sequence
<220> FEATURE:
<223> OTHER INFORMATION: Primer

<400> SEQUENCE: 18
ggatccatgg atcagctaac cagtgcc                                           27

<210> SEQ ID NO 19
<211> LENGTH: 33
<212> TYPE: DNA
<213> ORGANISM: Artificial sequence
<220> FEATURE:
<223> OTHER INFORMATION: Primer

<400> SEQUENCE: 19
gtcgacctaa aagaaccagg acgcggagtc act                                    33
```